US009572855B2

(12) United States Patent
Kufe et al.

(10) Patent No.: US 9,572,855 B2
(45) Date of Patent: Feb. 21, 2017

(54) COMBINATION ANTI-ESTROGEN RECEPTOR CANCER THERAPY USING MUC1 PEPTIDES AND CHEMOTHERAPEUTICS

(71) Applicants: DANA-FARBER CANCER INSTITUTE, INC., Boston, MA (US); GENUS ONCOLOGY, LLC, Chicago, IL (US)

(72) Inventors: Donald W. Kufe, Wellesley, MA (US); Surender Kharbanda, Natick, MA (US)

(73) Assignees: DANA-FARBER CANCER INSTITUTE, INC., Boston, MA (US); GENUS ONCOLOGY, LLC, Chicago, IL (US)

(*) Notice: Subject to any disclaimer, the term of this patent is extended or adjusted under 35 U.S.C. 154(b) by 15 days.

(21) Appl. No.: 14/774,163

(22) PCT Filed: Mar. 10, 2014

(86) PCT No.: PCT/US2014/022284
§ 371 (c)(1),
(2) Date: Sep. 10, 2015

(87) PCT Pub. No.: WO2014/164395
PCT Pub. Date: Oct. 9, 2014

(65) Prior Publication Data
US 2016/0058827 A1 Mar. 3, 2016

Related U.S. Application Data
(60) Provisional application No. 61/776,586, filed on Mar. 11, 2013.

(51) Int. Cl.
*A61K 38/10* (2006.01)
*A61K 38/07* (2006.01)
*A61K 38/08* (2006.01)
*A61K 38/17* (2006.01)
*A61K 31/138* (2006.01)

(52) U.S. Cl.
CPC ............. *A61K 38/07* (2013.01); *A61K 31/138* (2013.01); *A61K 38/08* (2013.01); *A61K 38/10* (2013.01); *A61K 38/1735* (2013.01)

(58) Field of Classification Search
CPC ........ A61K 38/10; A61K 38/07; A61K 38/08; G01N 2440/00
USPC .......... 514/19.3, 19.4, 19.5, 19.6, 21.4, 21.9
See application file for complete search history.

(56) References Cited

U.S. PATENT DOCUMENTS

| 8,524,669 B2 | 9/2013 | Kufe et al. |
| 8,614,186 B2 | 12/2013 | Kufe et al. |
| 8,957,185 B2 | 2/2015 | Kufe et al. |
| 9,096,687 B2 | 8/2015 | Kufe et al. |
| 2010/0125055 A1* | 5/2010 | Kufe ................. A61K 38/1735 514/1.1 |
| 2015/0353676 A1* | 12/2015 | Singh .................. A61K 31/704 424/497 |

FOREIGN PATENT DOCUMENTS

| WO | WO 2010/045586 | 4/2010 |
| WO | WO 2011/100688 | 8/2011 |

OTHER PUBLICATIONS

Arpino et al., "Crosstalk between the estrogen receptor and the HER tyrosine kinase receptor family: molecular mechanism and clinical implications for endocrine therapy resistance" Endocr Rev., 29:217-33, 2008.
De Laurentiis et al., "A meta-analysis on the interaction between HER-2 expression and response to endocrine treatment in advanced breast cancer," Clin Cancer Res., 11:4741-8, 2005.
Ellis et al., "Estrogen-independent proliferation is present in estrogen-receptor HER2-positive primary breast cancer after neoadjuvant letrozole," J. Clin. Oncol., 24:3019-25, 2006.
Jin et al., "Cooperative interaction between the MUC1-C oncoprotein and the Rab31 GTPase in estrogen receptor-positive breast cancer cells," PLoS One, 7:e39432, 2012.
Jin et al., "Targeting the eIF4A RNA helicase blocks translation of the MUC1-C oncoprotein," Oncogene, 32:2179-2188, 2013.
Kharbanda et al., "Oncogenic MUC1-C promotes tamoxifen resistance in human breast cancer," Molecular Cancer Research, 11(7):714-723, 2013.
Kufe, "MUC1-C oncoprotein as a target in breast cancer: activation of signaling pathways and therapeutic approaches" Oncogene, 32:1073-1081, 2013.
Li et al., "Heregulin targets gamma-catenin to the nucleolus by a mechanism dependent on the DF3/MUC1 oncoprotein" Mol. Cancer Res., 1:765-775, 2003.
Miller et al., "ERα-dependent E2F transcription can mediate resistance to estrogen deprivation in human breast cancer," Cancer Discov., 1:338-51, 2011.
Miller et al., "Hyperactivation of phosphatidylinositol-3 kinase promotes escape from hormone dependence in estrogen receptor-positive human breast cancer" J. Clin. Invest., 120:2406-13, 2010.
Miller et al., "Phosphatidylinositol 3-kinase and antiestrogen resistance in breast cancer," J. Clin. Oncol., 29:4452-61, 2011.
Musgrove et al., "Biological determinants of endocrine resistance in breast cancer," Nat. Rev. Cancer, 9:631-43, 2009.
Osborne et al., "Mechanisms of endocrine resistance in breast cancer," Annu. Rev. Med., 62:233-47, 2011.
PCT International Search Report and Written Opinion issued in International Patent Application No. PCT/US2014/022284, dated Jul. 17, 2014.

(Continued)

Primary Examiner — Julie Ha
(74) Attorney, Agent, or Firm — Parker Highlander PLLC

(57) ABSTRACT

The invention provides for treatment of MUC1+/ERα+/− cancers using an anti-MUC1 therapy, optionally including an anti-ERα therapy. In particular, the invention addresses the treatment of tamoxifen-resistant cancers, using MUC1+, and optionally anti-ERα therapy.

36 Claims, 9 Drawing Sheets

(56) References Cited

OTHER PUBLICATIONS

Pitroda et al., "MUC1-induced alterations in a lipid metabolic gene network predict response of human breast cancers to tamoxifen treatment" *Proc. Natl. Acad. Sci. USA*, 106:5837-41, 2009.

Raina et al., "Dependence on the MUC1-C oncoprotein in non-small cell lung cancer cells" *Mol. Cancer Therapeutics*, 10:806-16, 2011.

Raina et al., "Direct targeting of the mucin 1 oncoprotein blocks survival and tumorigenicity of human breast carcinoma cells," *Cancer Research*, 69(12):5133-5141, 2009.

Raina et al., "Targeting cysteine-mediated dimerization of the MUC1-C oncoprotein in human cancer cells," *International Journal of Oncology*, 40(5):1643-1649, 2012.

Raina et al., "The MUC1 oncoprotein activates the anti-apoptotic phosphoinositide 3-kinase/Akt and Bcl-xL pathways in rat 3Y1 fibroblasts," *J. Biol. Chem..*, 279:20607-12, 2004.

Ren et al., "MUC1 oncoprotein is targeted to mitochondria by heregulin-induced activation of c-Src and the molecular chaperone HSP90," *Oncogene*, 25:20-31, 2006.

Uchida et al., "Inhibition of the MUC1-C oncoprotein is synergistic with cytotoxic agents in the treatment of breast cancer cells," *Cancer Biology and Therapy*, 14(2):127-134, 2013.

Wei et al., "MUC1 oncoprotein stabilizes and activates estrogen receptor alpha," *Mol. Cell*, 21:295-305, 2006.

Yin et al., "Human MUC1 carcinoma antigen regulates intracellular oxidant levels and the apoptotic response to oxidative stress," *J. Biol. Chem.*, 278:35458-35464, 2003.

\* cited by examiner

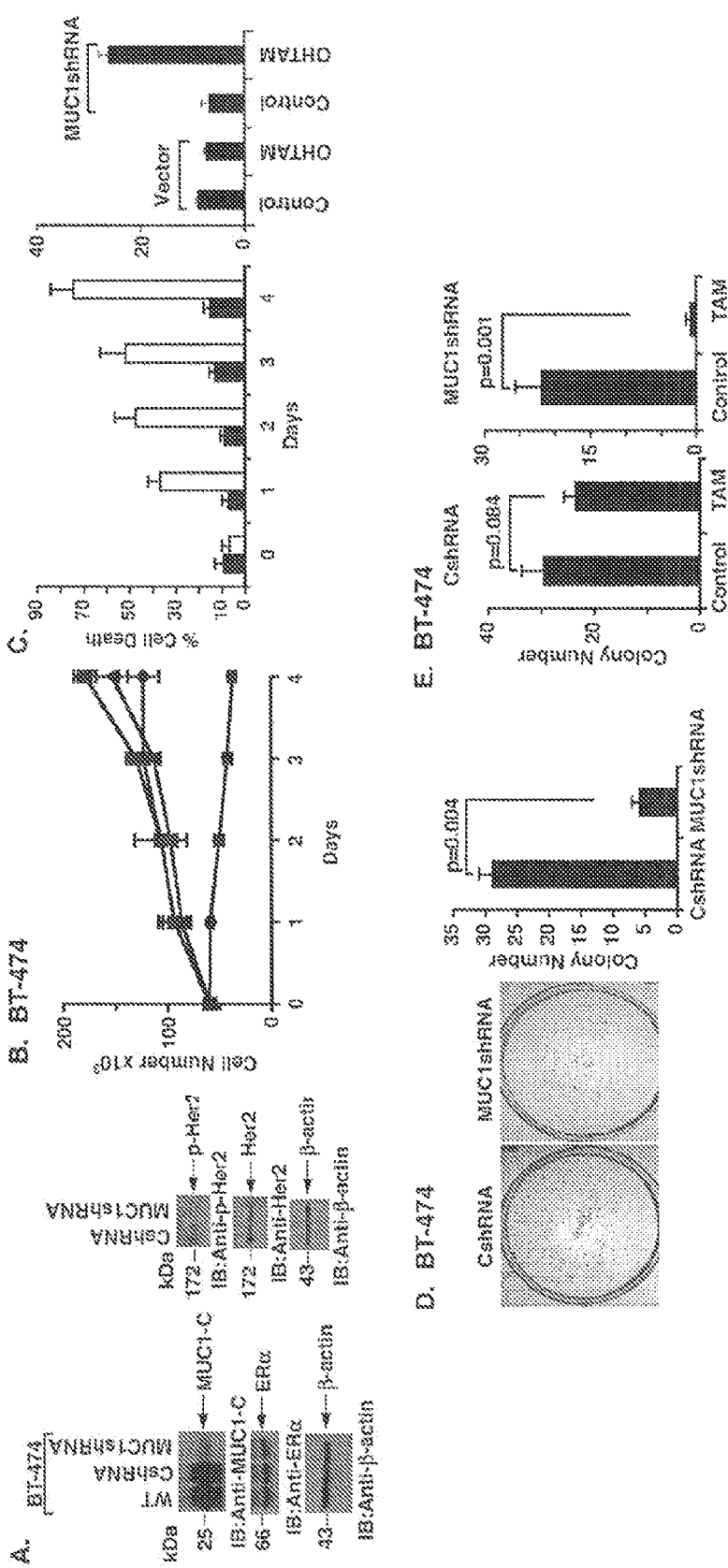
FIG. 1A-E

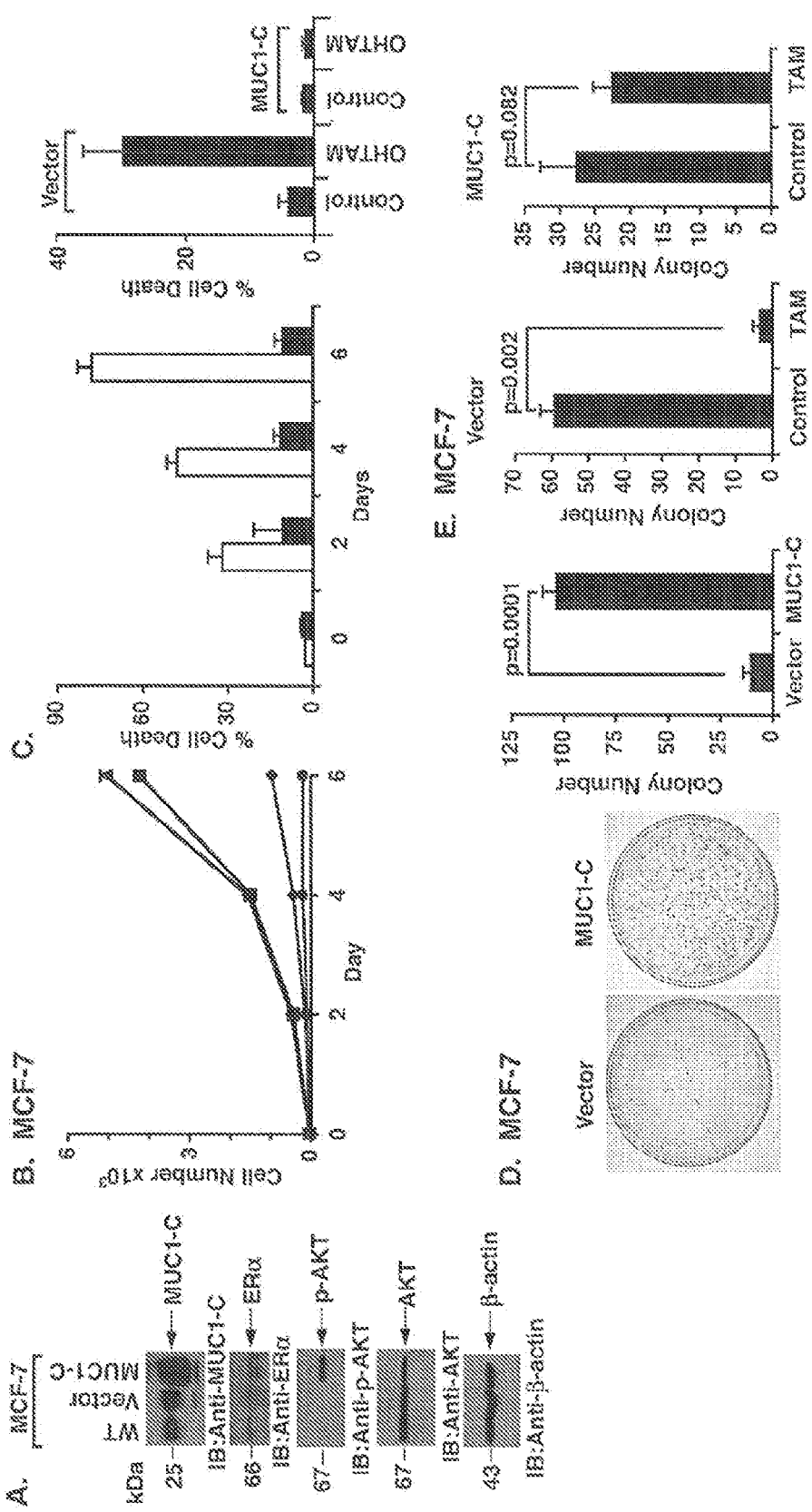
FIG. 2A-E

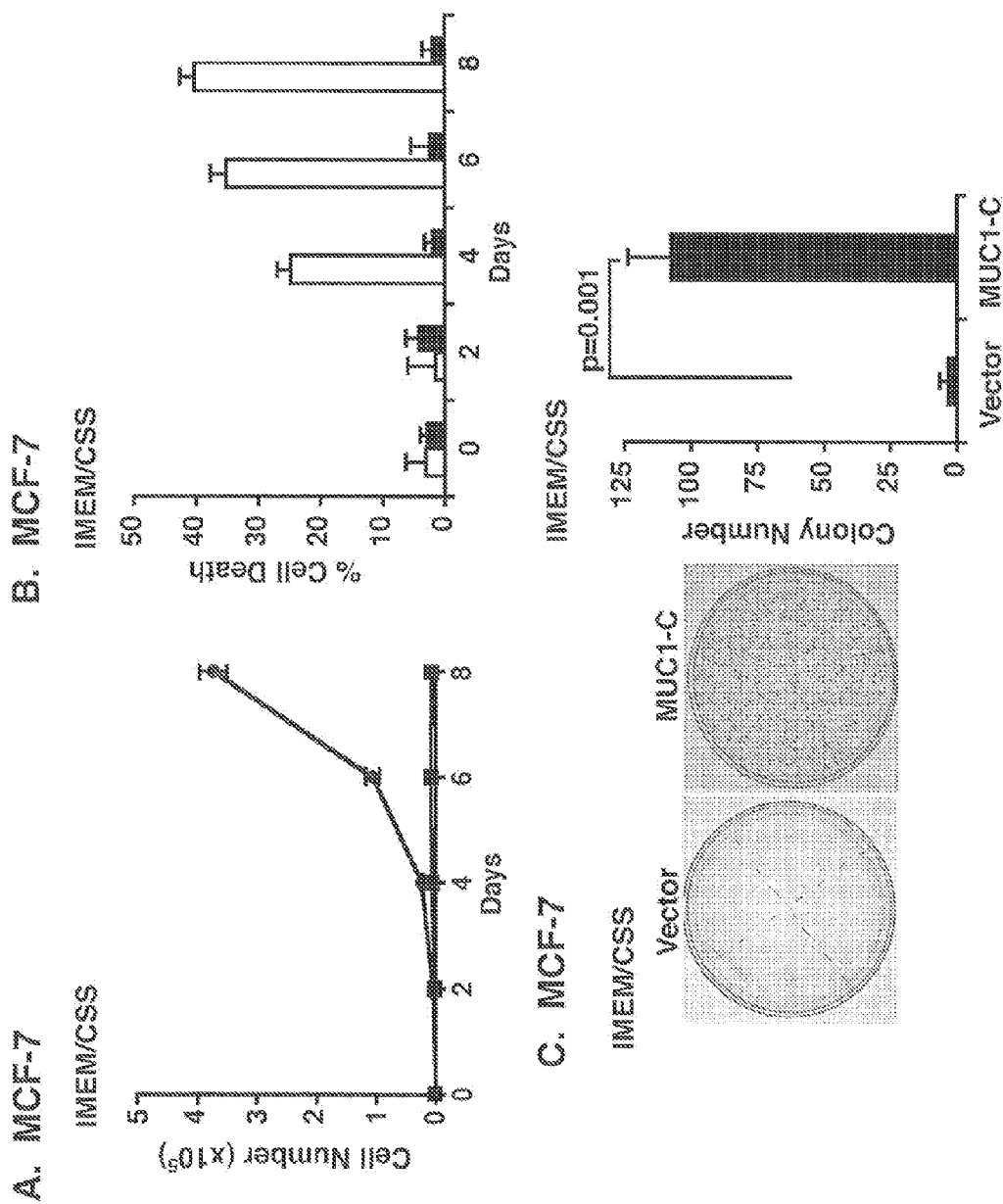
FIG. 3A-C

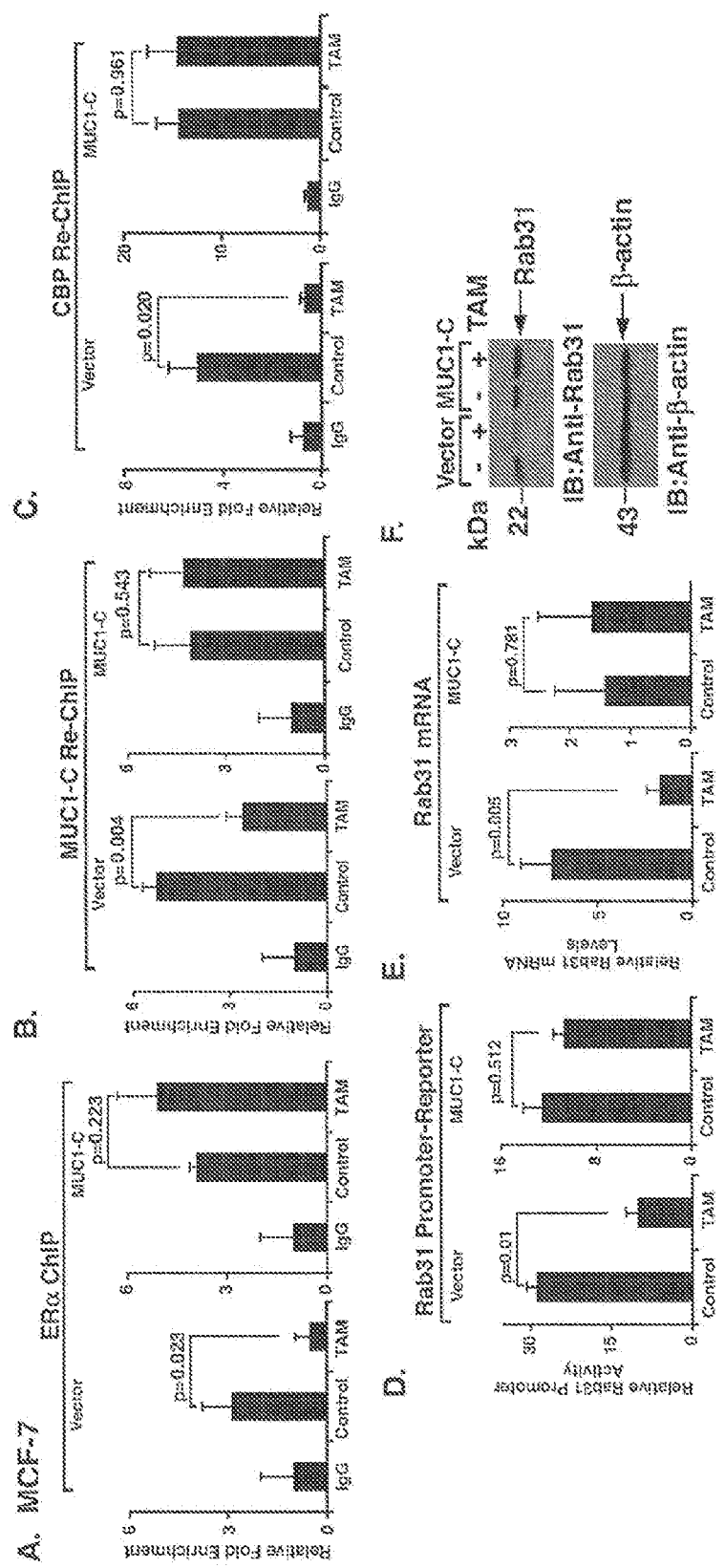
FIG. 4A-F

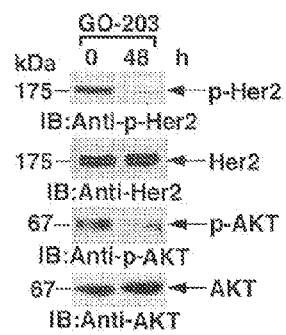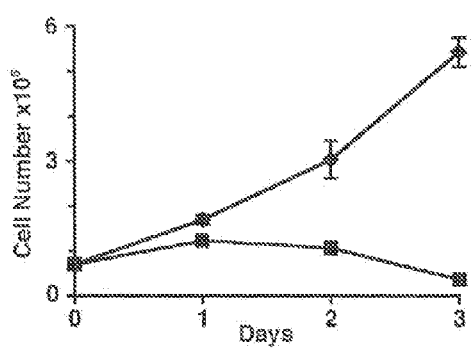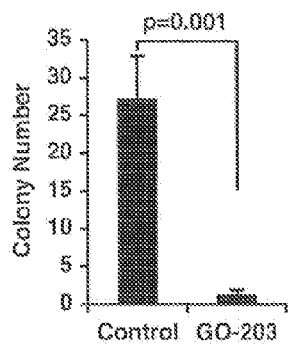
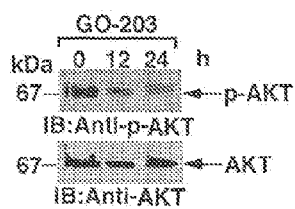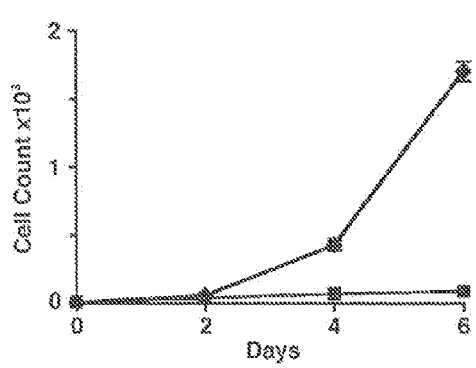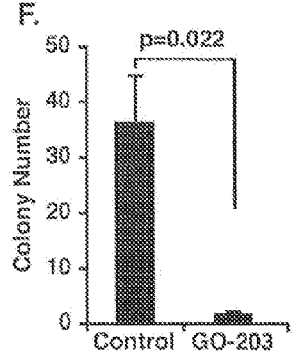
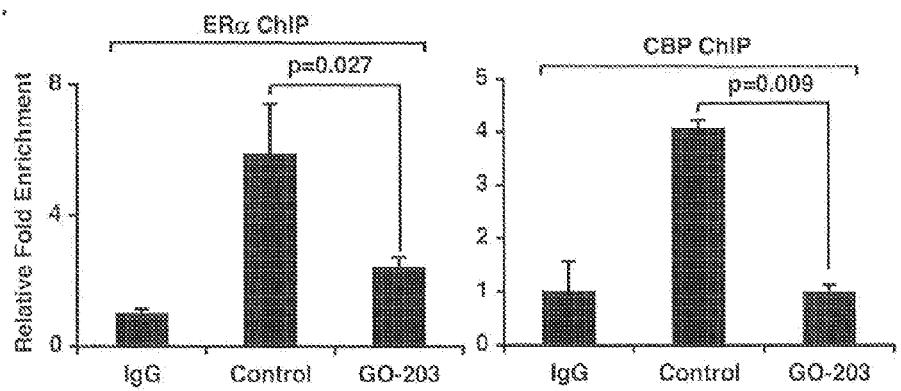
FIG. 5A-G

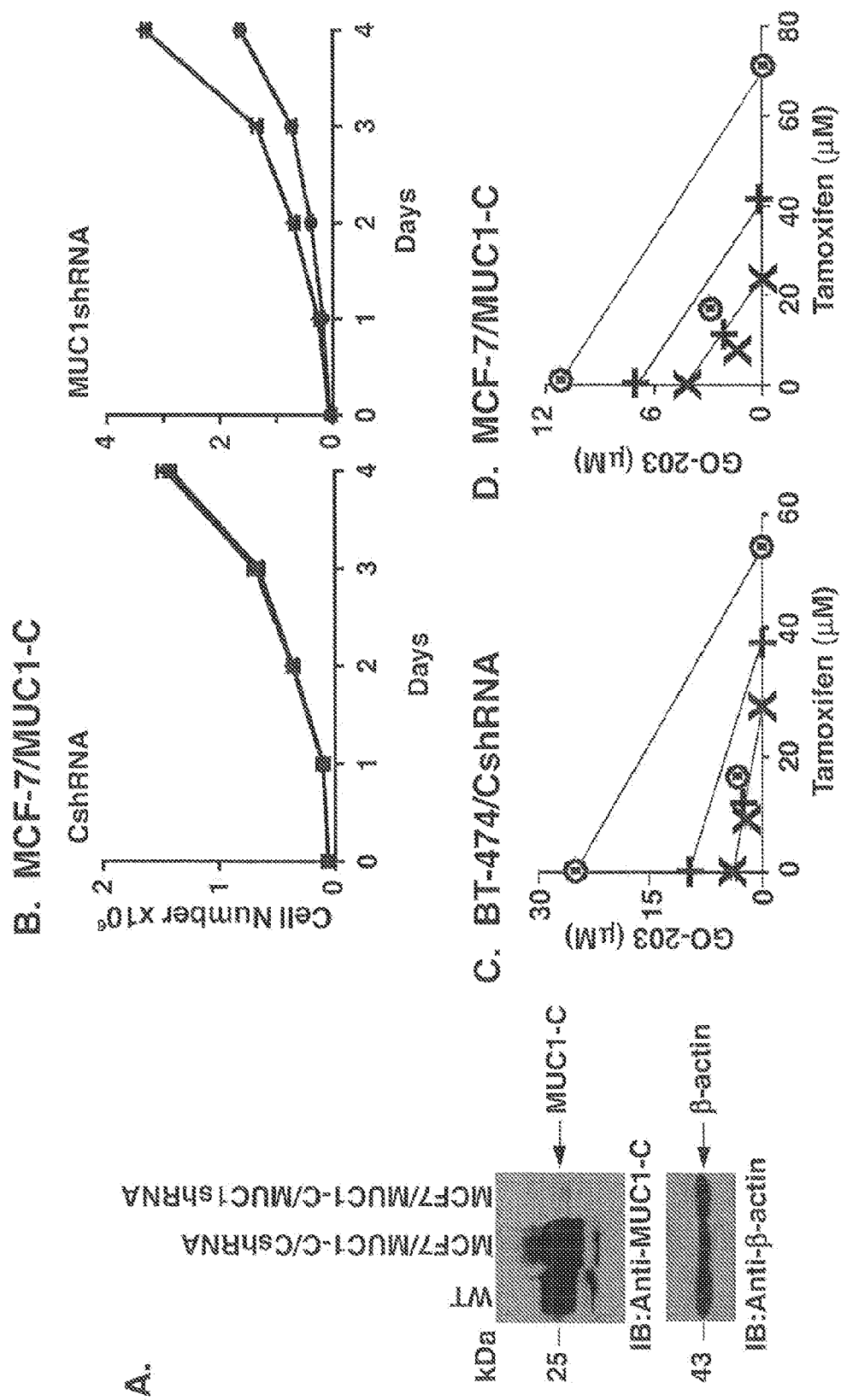
FIG. 6A-D

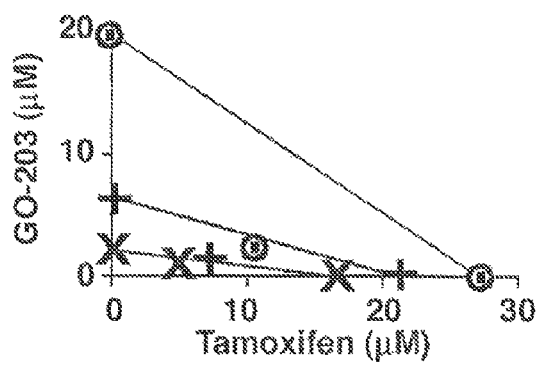 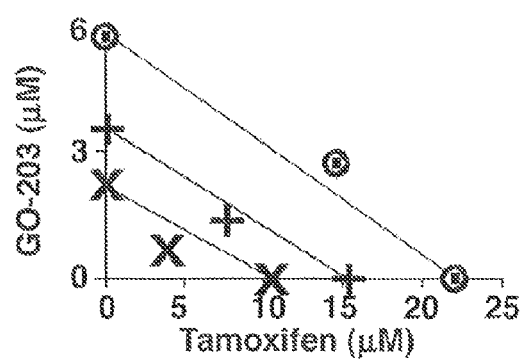
FIG. 9A-B

COMBINATION ANTI-ESTROGEN RECEPTOR CANCER THERAPY USING MUC1 PEPTIDES AND CHEMOTHERAPEUTICS

The application is a national phase application under 35 U.S.C. §371 of International Application No. PCT/US2014/022284, filed Mar. 10, 2014, which claims benefit of priority to U.S. Provisional Application Ser. No. 61/776,586, filed Mar. 11, 2013. The entire contents of the above-referenced disclosures are specifically incorporated herein by reference.

This invention was made with government support under grant numbers CA97098 and CA166480, awarded by the National Institutes of Health. The government has certain rights in the invention.

Pursuant to 37 C.F.R. 1.821(c), a sequence listing is submitted herewith as an ASCII compliant text file named "GENUP0036US_ST25.txt", created on Sep. 9, 2015 and having a size of ~16 kilobytes. The content of the aforementioned file is hereby incorporated by reference in its entirety.

BACKGROUND OF THE INVENTION

1. Field of the Invention

This invention relates to oncology and medicine, and more particularly to treatment of tamoxifen resistant cancers. In particular, MUC1 peptides derived from a particular region of the MUC1 cytoplasmic domain have been shown to inhibit MUC1 oligomerization and nuclear translocation, causing inhibition and even death of MUC1-expressing tumor cells, and these can be used advantageously in combination with ER-overexpressing cancers, as well as those that have developed resistant to ER-targeted therapies.

2. Related Art

The estrogen receptor α (ERα) signaling pathway contributes to the development and progression of human breast cancers. Over 70% of all breast cancers express ERα with a somewhat higher frequency in tumors from postmenopausal women (Osborne et al., 2011). Endocrine therapy of patients with ER+ breast cancer has included (i) blocking estrogen binding with selective ER modulators, such as tamoxifen, (ii) decreasing ER expression with fulvestrant, and (iii) inhibiting estrogen synthesis with aromatase inhibitors. These endocrine therapies have had a major impact on the natural history of hormone-dependent breast cancer; however, their effectiveness is often limited by intrinsic or acquired resistance (Osborne et al., 2011 and Musgrove et at., 2009). For example, adjuvant therapy of ER+ breast cancers with tamoxifen is associated with recurrent disease in about one-third of patients (Musgrove et al., 2009). One mechanism of acquired tamoxifen resistance is the down-regulation of ERα expression, although this response has been observed in only 15-20% of breast cancers (Gutierrez et al., 2005). Tamoxifen resistance has also been linked to cross-talk between ERα and receptor tyrosine kinases (RTKs), specifically epidermal growth factor receptor (EGFR), the epidermal growth factor receptor 2 (HER2/ERBB2) and the insulin-like growth factor receptor (IGF1-R) (Osborne et al., 2011; Musgrove et at., 2009). In this context, amplification and overexpression of HER2 has been associated with endocrine resistance (De Laurentiis et al., 2005, Ellis et al., 2006, Arpino et al., 2008). However, only about 10% of ER+ breast cancers overexpress HER2, indicating that additional mechanisms confer tamoxifen resistance in the majority of these tumors. Other work has shown that hyperactivation of the phosphatidylinositol 3-kinase (PI3K) pathway confers resistance to endocrine therapy through both direct and indirect ERα interactions (Miller et al., 2011). Accordingly, PI3K pathway inhibitors are being evaluated for the treatment of patients with tamoxifen-resistant ER+ breast cancer (Miller et al., 2011a). Nonetheless, new therapeutic targets are needed for the treatment of tamoxifen-resistant disease.

The mucin 1 (MUC1) heterodimeric protein is aberrantly overexpressed in about 90% of human breast cancers (Kufe, 2012). The two MUC1 subunits are generated by autocleavage of a single polypeptide and, in turn, form a stable non-covalent complex (Kufe, 2012; 2009). The MUC1 N-terminal subunit (MUC1-N) is the heavily glycosylated mucin component of the heterodimer. MUC1-N is positioned extracellularly in a complex at the cell membrane with the MUC1 C-terminal (MUC1-C) transmembrane subunit (Kufe, 2009). MUC1-C functions as an oncoprotein by interacting with RTKs, such as EGFR and HER2, at the breast cancer cell surface and by contributing to their downstream signaling pathways (Kufe, 2012). In this regard, the 72 amino acid MUC1-C cytoplasmic domain acts as a substrate for EGFR and other RTKs. The MUC1-C cytoplasmic domain also contains a YHPM motif, that when phosphorylated on tyrosine, functions as a binding site for PI3K SH2 domains and thereby activation of the PI3K→AKT pathway (Raina et al., 2004; Raina et al., 2011). The MUC1-C subunit is, in addition, targeted to the nucleus where it interacts with certain transcription factors (Kufe, 2009). Of relevance to breast cancer, MUC1-C associates with ERα and this interaction is stimulated by 17β-estradiol (E2) (Wei et al., 2006). MUC1-C binds directly to the ERα DNA binding domain and stabilizes ERα by blocking its ubiquitination and degradation. MUC1-C also enhances ERα promoter occupancy, increases recruitment of coactivators and stimulates ERα-mediated transcription (Wei et al., 2006). Notably, tamoxifen has no effect on MUC1-C/ERα complexes and MUC1-C antagonizes the inhibitory effects of tamoxifen on ERα-mediated transcription (Wei et al., 2006). In other studies, a MUC1-C-induced 38-gene set was applied to the analysis of a database obtained from ER+ breast cancer patients treated with tamoxifen and (i) demonstrated a strong association with ER-dependent signaling, and (ii) predicted failure to tamoxifen treatment, as measured by disease-free and overall survival (Pitroda et al., 2009). These findings have supported a potential link between MUC1-C and tamoxifen resistance; however, there has been no direct evidence to date for such an association.

SUMMARY OF THE INVENTION

Thus, in accordance with the present invention, there is provided a method of inhibiting a MUC1-positive/ERα-positive tumor cell in a subject comprising administering to said subject a MUC1 peptide of at least 4 consecutive MUC1 residues and no more than 20 consecutive MUC1 residues and comprising the sequence CQC (SEQ ID NO:4), wherein the amino-terminal cysteine of CQC is covered on its $NH_2$-terminus by at least one amino acid residue that need not correspond to the native MUC-1 transmembrane sequence, wherein said tumor cell exhibits primary resistance to tamoxifen. The method may further comprise the step of assessing the expression of MUC1 in a tumor cell of said subject prior to administering said peptide. The method may further comprise the step of assessing the expression of ERα in a tumor cell of said subject prior to administering said peptide. The subject may metastatic and/or recurrent cancer.

The MUC1-positive tumor cell may be a carcinoma cell, such as a prostate or breast carcinoma cell. The cancer cell may be a carcinoma cell, a leukemia cell or a myeloma cell. The carcinoma cell may be a prostate or breast carcinoma cell. The ERα may be overexpressed as compared to a similar non-cancerous cell. The peptide may be fused to a cell delivery domain, such as poly-D-R, poly-D-P or poly-D-K. The peptide may comprise all L amino acids, all D amino acids, or a mix of L and D amino acids. The peptide may comprise at least 5, 6, 7 or 8 consecutive MUC1 residues, and/or no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1. The peptide may be at least 8 residues in length, and at least two non-adjacent residues may form a bridge through their side chains. The bridge may comprise a linker, chemically modified side chains, or hydrocarbon stapling. The linker may comprise a modification that stabilizes an alpha-helical structure of said peptide.

Administering comprises intravenous, intra-arterial, intratumoral, subcutaneous, topical or intraperitoneal administration, or local, regional, systemic, or continual administration. Inhibiting may comprise inducing growth arrest of said tumor cell, apoptosis of said tumor cell and/or necrosis of a tumor tissue comprising said tumor cell. The method may further comprise administering to said subject an anti-ERα therapy, such as tamoxifen. The anti-ERα therapy may administered prior to said peptide, after said peptide or at the same time as said peptide. The subject may a human. The peptide may be administered at 0.1-500 mg/kg/d or at 10-100 mg/kg/d. The peptide may be administered daily, such as daily for 7 days, 2 weeks, 3 weeks, 4 weeks, one month, 6 weeks, 8 weeks, two months, 12 weeks, or 3 months. The peptide may be administered weekly, such as weekly for 2 weeks, 3 weeks, 4 weeks, 6 weeks, 8 weeks, 10 weeks, or 12 weeks.

In another embodiment, there is provided a method of treating a human subject having MUC1-positive/ERα-positive cancer comprising administering to said subject (a) a MUC1 peptide of at least 4 consecutive MUC1 residues and no more than 20 consecutive MUC1 residues and comprising the sequence CQC (SEQ ID NO:4), wherein the amino-terminal cysteine of CQC is covered on its NH$_2$-terminus by at least one amino acid residue that need not correspond to the native MUC-1 transmembrane sequence; and (b) an anti-ERα therapy. The anti-ERα therapy may be is tamoxifen. The MUC1 peptide and/or said anti-ERα therapy may be administered to said subject more than once. The subject may have previously received an anti-ERα therapy, or not have previously received an anti-ERα therapy.

The cancer may be recurrent and/or metastatic. The ERα and/or MUC1 may be overexpressed as compared to a similar non-cancerous cell. The cancer may be a carcinoma, a leukemia or a myeloma. The carcinoma may be a prostate or breast carcinoma. The anti-ERα therapy may be administered prior to said peptide, after said peptide or at the same time as said peptide. The method may further comprise the step of assessing the expression of MUC1 in a tumor cell of said subject prior to administering said peptide. The method may further comprise the step of assessing the expression of ERα in a tumor cell of said subject prior to administering said peptide. The method may improve the response rate to said anti-ERα therapy as compared to the anti-ERα therapy given alone, or reverses resistance to said anti-ERα therapy.

In yet another embodiment, there is provided a method of inhibiting a MUC1-positive tumor cell in a subject comprising administering to said subject a MUC1 peptide of at least 4 consecutive MUC1 residues and no more than 20 consecutive MUC1 residues and comprising the sequence CQC (SEQ ID NO:4), wherein the amino-terminal cysteine of CQC is covered on its NH$_2$-terminus by at least one amino acid residue that need not correspond to the native MUC-1 transmembrane sequence, wherein said tumor cell exhibits resistance to tamoxifen. The method may further comprise the step of assessing the expression of MUC1 in a tumor cell of said subject prior to administering said peptide. The method may further comprise the step of assessing the expression of ERα in a tumor cell of said subject prior to administering said peptide. The subject may metastatic and/or recurrent cancer.

The MUC1-positive tumor cell may be a carcinoma cell, a leukemia cell or a myeloma cell. The carcinoma cell may be a prostate or breast carcinoma cell. The cancer cell may be a carcinoma cell, a leukemia cell or a myeloma cell. The carcinoma cell may be a prostate or breast carcinoma cell. The ERα may be overexpressed as compared to a similar non-cancerous cell. The peptide may be fused to a cell delivery domain, such as poly-D-R, poly-D-P or poly-D-K. The peptide may comprise all L amino acids, all D amino acids, or a mix of L and D amino acids. The peptide may comprise at least 5, 6, 7 or 8 consecutive MUC1 residues, and/or no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1. The peptide may be at least 8 residues in length, and at least two non-adjacent residues may form a bridge through their side chains. The bridge may comprise a linker, chemically modified side chains, or hydrocarbon stapling. The linkers may comprise modifications that stabilize an alpha-helical structure of said peptide.

Administering comprises intravenous, intra-arterial, intratumoral, subcutaneous, topical or intraperitoneal administration, or local, regional, systemic, or continual administration. Inhibiting may comprise inducing growth arrest of said tumor cell, apoptosis of said tumor cell and/or necrosis of a tumor tissue comprising said tumor cell. The MUC1-positive tumor cell may be ERα-positive or ERα-negative. The method may further comprise administering to said subject an anti-ERα therapy that is not tamoxifen. The anti-ERα therapy may be administered prior to said peptide, after said peptide or at the same time as said peptide. The subject may a human. The peptide may be administered at 0.1-500 mg/kg/d or at 10-100 mg/kg/d. The peptide may be administered daily, such as daily for 7 days, 2 weeks, 3 weeks, 4 weeks, one month, 6 weeks, 8 weeks, two months, 12 weeks, or 3 months. The peptide may be administered weekly, such as weekly for 2 weeks, 3 weeks, 4 weeks, 6 weeks, 8 weeks, 10 weeks, or 12 weeks.

The method may further comprise the step of assessing the expression of MUC1 in a tumor cell of said subject prior to administering said peptide. The method may further comprise the step of assessing the expression of ERα in a tumor cell of said subject prior to administering said peptide. The subject may have metastatic and/or recurrent cancer. The peptide may be at least 8 residues in length, and at least two non-adjacent residues form a bridge through their side chains. The bridge may comprise a linker, chemically modified side chains, or hydrocarbon stapling. The linker may comprise a modification that stabilizes an alpha-helical structure of said peptide. The cancer cell may be a carcinoma cell, a leukemia cell or a myeloma cell. The carcinoma cell may be a prostate or breast carcinoma cell. The MUC1 may be overexpressed as compared to a similar non-cancerous cell.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed.

FIGS. 1A-E. Resistance of HER2-overexpressing BT-474 cells to tamoxifen is conferred by MUC1-C expression. (FIG. 1A) Lysates from wild-type (WT) BT-474 cells, BT-474/CshRNA and BT-474/MUC1shRNA cells were immunoblotted with the indicated antibodies (left and right). (FIG. 1B) Control BT-474/CshRNA (squares) and BT-474/MUC1shRNA (diamonds) cells were left untreated. BT-474/CshRNA (triangles) and BT-474/MUC1shRNA (circles) were also treated with 5 µM tamoxifen on days 0 and 2. Cell number is expressed as the mean±SD of three replicates. (FIG. 1C) BT-474/CshRNA (solid bars) and BT-474/MUC1shRNA (open bars) cells were treated with 5 µM tamoxifen (left) or 10 nM OHTAM (right) on days 0 and 2. The results (mean±SD of three replicates) are expressed as the percentage of cell death as determined by trypan blue staining on the indicated days (left) or on day 4 (right). (FIG. 1D) BT-474/CshRNA and BT-474/MUC1shRNA cells were seeded at 1000 cells/well (6-well plate), grown for 14 days and then stained with crystal violet (left). Colony number (>30 cells) is expressed as the mean±SD of three replicates (right). (FIG. 1E) BT-474/CshRNA (1000 cells/well; left) and BT-474/MUC1shRNA (2000 cells/well; right) cells were seeded in 6-well plates and left untreated (Control) or treated with 5 µM tamoxifen (TAM) every other day for 14 days. Colony number (>30 cells) is expressed as the mean±SD of three replicates.

FIGS. 2A-E. Overexpression of MUC1-C in MCF-7 cells is associated with tamoxifen resistance. (FIG. 2A) Lysates from wild-type (WT) MCF-7 cells, MCF-7/vector and MCF-7/MUC1-C cells were immunoblotted with the indicated antibodies. (FIG. 2B) Control MCF-7/vector (diamonds) and MCF-7/MUC1-C (triangles) cells were left untreated. MCF-7/vector (circles) and MCF-7/MUC1-C (squares) cells were also treated with 5 µM tamoxifen on days 0, 2 and 4. Cell number is expressed as the mean±SD of three replicates. (FIG. 2C) MCF-7/vector (open bars) and MCF-7/MUC1-C (solid bars) cells were treated with 5 µM tamoxifen on days 0, 2 and 4 (left) or 10 nM OHTAM on days 0 and 2 (right). The results (mean±SD of three replicates) are expressed as the percentage of cell death as determined by trypan blue staining on the indicated days (left) or on day 4 (right). (FIG. 2D) MCF-7/vector and MCF-7/MUC1-C cells were seeded at 500 cells/well (6-well plate), grown for 7 days and then stained with crystal violet (left). Colony number (>30 cells) is expressed as the mean±SD of three replicates (right). (FIG. 2E) MCF-7/vector (2000 cells/well; left) and MCF-7/MUC1-C (500 cells/well; right) cells were seeded in 6-well plates and left untreated (Control) or treated with 5 µM tamoxifen (TAM) every other day for 7 days. Colony number (>30 cells) is expressed as the mean±SD of three replicates.

FIGS. 3A-C. MCF-7 cells overexpressing MUC1-C are estrogen-independent. (FIG. 3A) MCF-7/vector (squares) and MCF-7/MUC1-C (circles) were seeded at $1\times10^4$ cells/ml in IMEM/CSS medium for the indicated number of days. The results are expressed as the cell number$\times10^5$/ml (mean±SD of three replicates). (FIG. 3B) MCF-7/vector (open bars) and MCF-7/MUC1-C (solid bars) cells were seeded in IMEM/CSS medium for the indicated number of days. The results are expressed as the percentage of cell death (mean±SD of three replicates) as determined by trypan blue staining. (FIG. 3C) MCF-7/vector and MCF-7/MUC1-C cells were seeded at 500 cells/well (6-well plate), grown for 7 days in IMEM/CSS medium and then stained with crystal violet (left). Colony number (>30 cells) is expressed as the mean±SD of three replicates (right).

FIGS. 4A-F. MUC1-C blocks the effects of tamoxifen on occupancy and activation of the Rab31 promoter. (FIGS. 4A-C) MCF-7/vector (left) and MCF-7/MUC1-C (right) cells were left untreated (Control) or treated with 5 µM tamoxifen for 2 days. (FIG. 4A) Soluble chromatin was precipitated with anti-ERα or a control IgG. The precipitates were analyzed for Rab31 promoter estrogen-responsive element (ERE) or control region (CR) sequences (16). The results (mean±SD of three determinations) are expressed as the relative fold enrichment compared to that obtained with the IgG control. (FIGS. 4B-C) In re-ChIP experiments, the anti-ERα precipitates were released, reimmunoprecipitated with anti-MUC1-C (FIG. 4B) or anti-CBP (FIG. 4C) and a control IgG, and then analyzed for Rab31 promoter sequences. The results (mean±SD of three determinations) are expressed as the relative fold enrichment compared to that obtained with the IgG control. (FIG. 4D) MCF-7/vector and MCF-7/MUC1-C cells were transfected with the pGL3 vector or pRab31-Luc and Renilla plasmid as an internal control. The cells were then left untreated (control) or treated with 5 µM tamoxifen for 2 days and then assayed for luciferase activity. The results (mean±SD of three determinations) are expressed as the relative Rab31 promoter activity as compared to that obtained for cells transfected with the pGL3 vector. (FIG. 4E) MCF-7/vector and MCF-7/MUC1-C cells were left untreated (Control) or treated with 5 µM tamoxifen for 2 days. Rab31 and GAPDH mRNA levels were determined by qRT-PCR. The results (mean±SD of three replicates) are expressed as relative Rab31 mRNA levels as compared to that obtained for GAPDH. (FIG. 4F) Lysates from the indicated cells were immunoblotted with anti-Rab31 and anti-β-actin.

FIGS. 5A-G. Tamoxifen-resistant cells are sensitive to MUC1-C inhibition. (FIG. 5A) BT-474 cells were left untreated (Control) or treated with 5 µM GO-203 each day for 2 days. Lysates were immunoblotted with the indicated antibodies. (FIG. 5B) BT-474/CshRNA cells were left untreated (diamonds) or treated with 5 μM GO-203 (squares) each day for the indicated days. The results (mean±SD of three replicates) are expressed as the viable cell number. (FIG. 5C) BT-474/CshRNA cells were seeded at 1000 cells/well in 6-well plates and left untreated (Control) or treated with 5 μM GO-203 each day for 7 days. Colony number (>30 cells) is expressed as the mean±SD of three replicates. D. MCF-7/MUC1-C cells were left untreated (Control) or treated with 5 μM GO-203 each day for 2 days. Lysates were immunoblotted with the indicated antibodies. (FIG. 5E) MCF-7/MUC1-C cells were left untreated (diamonds) or treated with 5 μM GO-203 (squares) each day for the indicated days. The results (mean±SD of three replicates) are expressed as the viable cell number. (FIG. 5F) MCF-7/MUC1-C cells were seeded at 200 cells/well in 6-well plates and left untreated (Control) or treated with 5 μM GO-203 each day for 7 days. Colony number (>30 cells) is expressed as the mean±SD of three replicates. (FIG. 5G) MCF-7/MUC1-C cells were left untreated (Control) or treated with 5 μM GO-203 each day for 2 days. Soluble chromatin was precipitated with anti-ERα (left), anti-CBP (right) or a control IgG. The precipitates were analyzed for Rab31 promoter sequences. The results (mean±SD of three determinations) are expressed as the relative fold enrichment compared to that obtained with the IgG control.

FIGS. 6A-D. Synergistic interaction between GO-203 and tamoxifen. (FIG. 6A) MCF-7/MUC1-C cells were infected with lentiviruses expressing the control shRNA (CshRNA) or the MUC1shRNA. Lysates from wild-type (WT) MCF-7 cells, MCF-7/MUC1-C/CshRNA and MCF-7/MUC1-C/MUC1shRNA cells were immunoblotted with the indicated antibodies. (FIG. 6B) MCF-7/MUC1-C/CshRNA (left) and MCF-7/MUC1-C/MUC1shRNA (right) cells were left untreated (triangle) or treated (circle) with 5 μM tamoxifen days 0 and 2. The results (mean±SD of three replicates) are expressed as viable cell number. (FIGS. 6C-D) BT-474/CshRNA (FIG. 6C) and MCF-7/MUC1-C (FIG. 6D) cells were treated with fixed IC50 ratios of (i) GO-203 alone on days 0, 1, 2, 3 and 4, (ii) tamoxifen alone on days 0, 2 and 4 and (iii) the GO-203/tamoxifen combination. For tamoxifen-resistant BT-474/CshRNA and MCF-7/MUC1-C cells, tamoxifen was used at the half-maximal inhibitory concentrations obtained for the tamoxifen-sensitive BT-474/MUC1shRNA and MCF-7/vector cells, respectively. The multiple effect-level isobologram analyses are shown for the $ED_{50}$ (X), $ED_{75}$ (+) and $ED_{90}$ (○) values.

FIGS. 9A-B. BT474/MUC1shRNA (FIG. 9A) and MCF-7/vector (FIG. 9B) cells were treated with fixed IC50 ratios of (i) GO-203 alone on days 0, 1, 2, 3 and 4, (ii) tamoxifen alone on days 0, 2 and 4 and (iii) the GO-203/tamoxifen combination. For tamoxifen-resistant BT-474/CshRNA and MCF-7/MUC1-C cells, tamoxifen was used at the half-maximal inhibitory concentrations obtained for the tamoxifen-sensitive BT-474/MUC1shRNA and MCF-7/vector cells, respectively. The multiple effect-level isobologram analyses are shown for the $ED_{50}$ (X), $ED_{75}$ (+) and $ED_{90}$ (○) values.

DESCRIPTION OF ILLUSTRATIVE EMBODIMENTS

Figure 7:
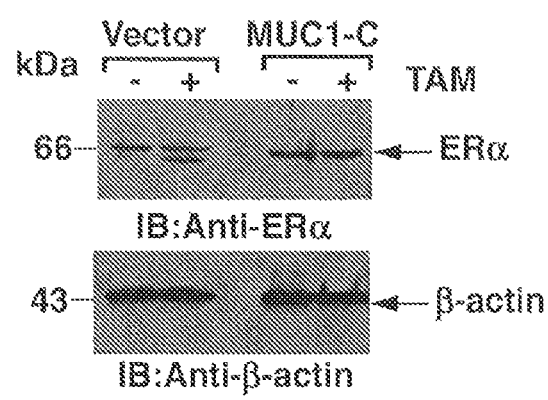
FIG. 7. MCF-7/vector and MCF-7/MUC1-C cells were left untreated or treated with 5 μM tamoxifen for 2 days. Lysates were immunoblotted with the indicated antibodies.

MUC1 has been studied extensively by the inventors and others for its role in cancer. As discussed above, human MUC1 is heterodimeric glycoprotein, translated as a single polypeptide and cleaved into N- and C-terminal subunits in the endoplasmic reticulum (Ligtenberg et al., 1992; Macao et al., 2006; Levitan et al., 2005). Aberrant overexpression of MUC1, as found in most human carcinomas (Kufe et al., 1984), confers anchorage-independent growth and tumorigenicity (Li et al., 2003a; Huang et al., 2003; Schroeder et al., 2004; Huang et al., 2005). Other studies have demonstrated that overexpression of MUC1 confers resistance to apoptosis induced by oxidative stress and genotoxic anticancer agents (Yin and Kufe, 2003b; Ren et al., 2004; Raina et al., 2004; Yin et al., 2004; Raina et al., 2006; Yin et al., 2007).

The family of tethered and secreted mucins functions in providing a protective barrier of the epithelial cell surface. With damage to the epithelial layer, the tight junctions between neighboring cells are disrupted, and polarity is lost as the cells initiate a heregulin-induced repair program (Vermeer et al., 2003). MUC1-N is shed from the cell surface (Abe and Kufe, 1989), leaving MUC1-C to function as a transducer of environmental stress signals to the interior of the cell. In this regard, MUC1-C forms cell surface complexes with members of the ErbB receptor family, and MUC1-C is targeted to the nucleus in the response to heregulin stimulation (Li et al., 2001; Li et al., 2003c). MUC1-C also functions in integrating the ErbB receptor and Wnt signaling pathways through direct interactions between the MUC1 cytoplasmic domain (CD) and members of the catenin family (Huang et al., 2005; Li et al., 2003c; Yamamoto et al., 1997; Li et al., 1998; Li et al., 2001; Li and Kufe, 2001). Other studies have demonstrated that MUC1-CD is phosphorylated by glycogen synthase kinase 3β, c-Src, protein kinase Cδ, and c-Abl (Raina et al., 2006; Li et al., 1998; Li et al., 2001; Ren et al., 2002).

The mechanisms responsible for nuclear targeting of MUC1-C are unclear. Proteins containing a classical nuclear localization signal (NLS) are imported into the nucleus by first binding to importin α and then, in turn, importin β (Weis, 2003). The cargo-importin α/β complex docks to the nuclear pore by binding to nucleoporins and is transported through the pore by a mechanism dependent on the Ran GTPase. Classical NLSs are monopartite with a single cluster of 4-5 basic amino acids or bipartite with two clusters of basic amino acids separated by a linker of 10-12 amino acids. MUC1-CD contains a RRK motif that does not conform to a prototypical monopartite NLS (Hodel et al., 2002). However, certain proteins containing non-classical NLSs are transported through the nuclear pore by binding directly to importin β (Kau et al., 2004). Importin β associates with several nucleoporins (Ryan and Wente, 2000), including Nup62, which is located on both the cytoplasmic and nucleoplasmic faces of nuclear pore complexes (Percipalle et al., 1997). Other studies have indicated that β-catenin is imported into the nucleus by an importin- and nucleoporin-independent mechanism (Suh and Gumbiner, 2003).

In 2006, the inventors reported that MUC1 is imported into the nucleus by a mechanism involving binding to Nup62. They also demonstrated that MUC1 forms oligomers through a CQC motif in the MUC1 cytoplasmic domain and that MUC1 oligomerization is necessary for nuclear import. In 2009, they extended this work to encompass a further understanding of the role that the CQC motif plays in oligomer formation. They demonstrated that short peptides corresponding to this region are able to disrupt MUC1 oligomer formation, preventing transport into the nucleus of tumor cells. These peptides were able to inhibit tumor cell growth, as well as induce apoptosis in such cells and even necrosis of tumor tissue.

Here, in studies using BT-474 cells, the inventors demonstrate that silencing MUC1-C is associated with sensitivity to tamoxifen-induced growth inhibition and loss of clonogenic survival. In concert with these results, overexpression of MUC1-C in MCF-7 cells confers tamoxifen resistance. They also show that MUC1-C forms complexes with ERα on the estrogen-responsive promoter of the Rab31 gene and that MUC1-C blocks tamoxifen-induced decreases in ERα occupancy. MUC1-C also attenuated tamoxifen-induced decreases in (i) recruitment of the coactivator CREB binding protein, (ii) Rab31 promoter activation, and (ii) Rab31 mRNA and protein levels. The importance of MUC1-C is further supported by the demonstration that targeting MUC1-C in combination with tamoxifen is highly synergistic in the treatment of tamoxifen-resistant breast cancer cells. The present studies using loss and gain of MUC1-C function demonstrate that MUC1-C is sufficient to confer tamoxifen resistance in breast cancer cells. The mechanistic basis for these results is supported by the demonstration that MUC1-C (i) contributes to HER2 and AKT activation, and (ii) blocks tamoxifen-induced decreases in ERα occupancy on an estrogen-responsive promoter. The results also demonstrate that targeting MUC1-C is synergistic with tamoxifen in the treatment of tamoxifen-resistant breast cancer cells.

I. Muc1

A. Structure

MUC1 is a mucin-type glycoprotein that is expressed on the apical borders of normal secretory epithelial cells (Kufe et al., 1984). MUC1 forms a heterodimer following synthesis as a single polypeptide and cleavage of the precursor into two subunits in the endoplasmic reticulum (Ligtenberg et al., 1992). The cleavage may be mediated by an autocatalytic process (Levitan et al., 2005). The >250 kDa MUC1 N-terminal (MUC1 N-ter, MUC1-N) subunit contains variable numbers of 20-amino acid tandem repeats that are imperfect with highly conserved variations and are modified by O-linked glycans (Gendler et al., 1988; Siddiqui et al., 1988). MUC1-N is tethered to the cell surface by dimerization with the ~23 kDa C-terminal subunit (MUC1 C-ter, MUC1-C), which includes a 58-amino acid extracellular region, a 28-amino acid transmembrane domain and a 72-amino acid cytoplasmic domain (CD; SEQ ID NO:1) (Merlo et al., 1989). The human MUC1 sequence is shown below:

GSVVVQLTLAFREGTINVHDVETQFNQYKTEAASRYNLTISDVSVSDVP

FPFSAQSGAGVPGWGIALLVLVCVLVALAIVYLIALAVCQCRRKNYGQL

DIFPARDTYHPMSEYPTYHTHGRYVPPSSTDRSPYEKVSAGNGGSSLSY

TNPAVAATSANL

The bold sequence indicates the CD (SEQ ID NO: 2), and the underlined portion is an oligomer-inhibiting peptide (SEQ ID NO:3) described in the examples.

With transformation of normal epithelia to carcinomas, MUC1 is aberrantly overexpressed in the cytosol and over the entire cell membrane (Kufe et al., 1984; Perey et al., 1992). Cell membrane-associated MUC1 is targeted to endosomes by clathrin-mediated endocytosis (Kinlough et al., 2004). In addition, MUC1-C, but not MUC1-N, is targeted to the nucleus (Baldus et al., 2004; Huang et al., 2003; Li et al., 2003a; Li et al., 2003b; Li et al., 2003c; Wei et al., 2005; Wen et al., 2003) and mitochondria (Ren et al., 2004).

II. ER-Expressing and -Overexpressing Cancers

A. ER in Cancer

Estrogen receptors are a group of proteins found inside cells. They are receptors that are activated by the hormone estrogen (17β-estradiol). Two classes of estrogen receptor exist: ER, which is a member of the nuclear hormone family of intracellular receptors, and the estrogen G protein-coupled receptor GPR30 (GPER), which is a G protein-coupled receptor. Once activated by estrogen, the estrogen receptor is able to bind to DNA and regulate the activity of many different genes (i.e., it is a DNA-binding transcription factor). However, it also has additional functions independent of DNA binding.

There are two different forms of the estrogen receptor, usually referred to as α and β, each encoded by a separate gene (ESR1 and ESR2, respectively). Hormone-activated estrogen receptors form dimers, and, since the two forms are coexpressed in many cell types, the receptors may form ERα (αα) or ERβ (ββ) homodimers or ERαβ (αβ) heterodimers. Estrogen receptor α and β show significant overall sequence homology, and both are composed of five domains (listed from the N- to C-terminus; amino acid sequence numbers refer to human ER):(A-F domain).

The N-terminal A/B domain is able to transactivate gene transcription in the absence of bound ligand (e.g., the estrogen hormone). While this region is able to activate gene transcription without ligand, this activation is weak and more selective compared to the activation provided by the E domain. The C domain, also known as the DNA-binding domain, binds to estrogen response elements in DNA. The D domain is a hinge region that connects the C and E domains. The E domain contains the ligand binding cavity as well as binding sites for coactivator and corepressor proteins. The E-domain in the presence of bound ligand is able to activate gene transcription. The C-terminal F domain function is not entirely clear and is variable in length.

Due to alternative RNA splicing, several ER isoforms are known to exist. At least three ERα and five ERβ isoforms have been identified. The ERβ isoforms receptor subtypes can transactivate transcription only when a heterodimer with the functional ERβ1 receptor of 59 kDa is formed. The ERβ3 receptor was detected at high levels in the testis. The two other ERα isoforms are 36 and 46 kDa.

Estrogen receptors are over-expressed in around 70% of breast cancer cases, referred to as "ER-positive," and can be demonstrated in such tissues using immunohistochemistry. Two hypotheses have been proposed to explain why this causes tumorigenesis, and the available evidence suggests that both mechanisms contribute. First, binding of estrogen to the ER stimulates proliferation of mammary cells, with the resulting increase in cell division and DNA replication, leading to mutations. Second, estrogen metabolism produces genotoxic waste. The result of both processes is disruption of cell cycle, apoptosis and DNA repair, and, therefore, tumour formation. ERα is certainly associated with more differentiated tumors, while evidence that ERβ is involved is controversial. Different versions of the ESR1 gene (encoding ERα), have been identified (with single-nucleotide polymorphisms) and are associated with different risks of developing breast cancer.

Endocrine therapy for breast cancer involves selective estrogen receptor modulators (SERMS), such as tamoxifen, which behave as ER antagonists in breast tissue, or aromatase inhibitors, such as anastrozole. ER status is used to determine sensitivity of breast cancer lesions to tamoxifen and aromatase inhibitors Another SERM, raloxifene, has been used as a preventive chemotherapy for women judged to have a high risk of developing breast cancer. Another chemotherapeutic anti-estrogen, ICI 182,780 (Faslodex), which acts as a complete antagonist, also promotes degradation of the estrogen receptor.

B. MUC1 and ERα

As discussed above, MUC1-C associates with ERα and this interaction is stimulated by 17β-estradiol (E2) (14). MUC1-C binds directly to the ERα DNA binding domain and stabilizes ERα by blocking its ubiquitination and degradation. MUC1-C also enhances ERα promoter occupancy, increases recruitment of coactivators and stimulates ERα-mediated transcription (14). Notably, tamoxifen had no effect on MUC1-C/ERα complexes and MUC1-C antagonized the inhibitory effects of tamoxifen on ERα-mediated transcription (14). In other studies, a MUC1-C-induced 38-gene set was applied to the analysis of a database obtained from ER+ breast cancer patients treated with tamoxifen and (i) demonstrated a strong association with ER-dependent signaling, and (ii) predicted failure to tamoxifen treatment, as measured by disease-free and overall survival (15).

III. MUC1 Peptides

A. Structure

The present invention contemplates the design, production and use of various MUC1 peptides. The structural features of these peptides are as follows. First, the peptides have no more than 20 consecutive residues of MUC1. Thus, the term "a peptide having no more than 20 consecutive residues," even when including the term "comprising," cannot be understood to comprise a greater number of consecutive MUC1 residues. Second, the peptides will contain the CQC motif, and may also include the CQCR motif, CQCRR motif and the CQCRRK motif. Thus, the peptides will have, at a minimum, these three consecutive residues of the MUC1-C domain. Third, the peptides will have at least one amino acid residue attached to the NH$_2$-terminal side of the first C residue in the CQC motif, such that the first C residue is "covered" by that at least one amino acid attached thereto. This residue may be native to MUC1 (i.e., from the transmembrane domain), may be selected at random (any of the 20 naturally-occurring amino acids or analogs thereof), or may be part of another peptide sequence (e.g., a tag sequence for purification, a stabilizing sequence, or a cell delivery domain).

In general, the peptides will be 50 residues or less, again, comprising no more than 20 consecutive residues of MUC1. The overall length may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues. Ranges of peptide length of 4-50 residues, 5-50 residues, 6-50 residues, 7-50 residues, 7-25, residues, 4-20 residues, 5-20 residues, 6-20 residues, 7-20 residues, and 7-15 residues are contemplated. The number of consecutive MUC1 residues may be 4, 5, 6, 7, 8, 9, 10, 11, 12, 13, 14, 15, 16, 17, 18, 19 or 20. Ranges of consecutive residues of 4-20 residues, 5-20 residues, 6-20 residues, 7-20 residues and 4-15 residues, 5-15, residues, 6-15 residues or 7-15 residues are contemplated.

The present invention may utilize an L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally-occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

As mentioned above, the present invention contemplates fusing or conjugating a cell delivery domain (also called a cell delivery vector, or cell transduction domain). Such domains are well known in the art and are generally characterized as short amphipathic or cationic peptides and peptide derivatives, often containing multiple lysine and arginine resides (Fischer, 2007). Of particular interest are poly-D-Arg and poly-D-Lys sequences (e.g., dextrorotary residues, eight residues in length), while others are shown in Table 1, below.

TABLE 1

| CDD/CTD PEPTIDES | SEQ ID NO |
|---|---|
| QAATATRGRSAASRPTERPRAPARSASRPRRPVE | 5 |
| RQIKIWFQNRRMKWKK | 6 |
| RRMKWKK | 7 |
| RRWRRWWRRWWRRWRR | 8 |
| RGGRLSYSRRRFSTSTGR | 9 |
| YGRKKRRQRRR | 10 |
| RKKRRQRRR | 11 |
| YARAAARQARA | 12 |
| RRRRRRRR | 13 |
| KKKKKKKK | 14 |
| GWTLNSAGYLLGKINLKALAALAKXIL | 15 |
| LLILLRRRIRKQANAHSK | 16 |
| SRRHHCRSKAKRSRHH | 17 |
| NRARRNRRRVR | 18 |
| RQLRIAGRRLRGRSR | 19 |
| KLIKGRTPIKFGK | 20 |
| RRIPNRRPRR | 21 |
| KLALKLALKALKAALKLA | 22 |

TABLE 1-continued

| CDD/CTD PEPTIDES | SEQ ID NO |
|---|---|
| KLAKLAKKLAKLAK | 23 |
| GALFLGFLGAAGSTNGAWSQPKKKRKV | 24 |
| KETWWETWWTEWSQPKKKRKV | 25 |
| GALFLGWLGAAGSTMGAKKKRKV | 26 |
| MGLGLHLLVLAAALQGAKSKRKV | 27 |
| AAVALLPAVLLALLAPAAANYKKPKL | 28 |
| MANLGYWLLALFVTMWTDVGLCKKRPKP | 29 |
| LGTYTQDFNKFHTFPQTAIGVGAP | 30 |
| DPKGDPKGVTVTVTVTGKGDPXPD | 31 |
| PPPPPPPPPPPPPP | 32 |
| VRLPPPVRLPPPVRLPPP | 33 |
| PRPLPPPRPG | 34 |
| SVRRRPRPPYLPRPRPPPFFPPRLPPRIPP | 35 |
| TRSSRAGLQFPVGRVHRLLRK | 36 |
| GIGKFLHSAKKFGKAFVGEIMNS | 37 |
| KWKLFKKIEKVGQNIRDGIIKAGPAVAVVGQATQIAK | 38 |
| ALWMTLLKKVLKAAAKAALNAVLVGANA | 39 |
| GIGAVLKVLTTGLPALISWIKRKRQQ | 40 |
| INLKALAALAKKIL | 41 |
| GFFALIPKIISSPLPKTLLSAVGSALGGSGGQE | 42 |
| LAKWALKQGFAKLKS | 43 |
| SMAQDIISTIGDLVKWIIQTVNXFTKK | 44 |
| LLGDFFRKSKEKIGKEFKRIVQRIKQRIKDFLANLVPRTES | 45 |
| LKKLLKKLLKKLLKKLLKKL | 46 |
| KLKLKLKLKLKLKLKL | 47 |
| PAWRKAFRWAWRMLKKAA | 48 |

Also as mentioned above, peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino- and/or carboxyl-terminal residues.

B. Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids can can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

C. Linkers

Linkers or cross-linking agents may be used to fuse MUC1 peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge the physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al. (2000).

D. Design, Variants and Analogs

The present invention focuses on peptides comprising the sequence CQC. Having identified this key structure in MUC1 oligomer formation, the inventors also contemplate that variants of the CQC sequence may be employed. For example, certain non-natural amino acids that satisfy the structural constraints of the CQC sequence may be substituted without a loss, and perhaps with an improvement in, biological function. In addition, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

Also of interest are peptidomimetic compounds that are designed based upon the amino acid sequences of compounds of the invention that are peptides. Peptidomimetic compounds are synthetic compounds having a three-dimensional conformation "motif" that is substantially the same as the three-dimensional conformation of a selected peptide. The peptide motif provides the peptidomimetic compound with the ability to inhibit the oligomerization of MUC1. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

IV. Therapies

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render materials stable and allow for uptake by target cells. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Cancer Types and Subjects

Cancer cells to which the methods of the present invention can be applied include generally any cell that expresses MUC1 and ERα, or that overexpress MUC1, and are either ERα-positive or -negative. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

C. Treatment Methods

Peptides or analogs that inhibit MUC1 oligomer formation are generally useful as anti-cancer therapeutics or prophylactics. They can be administered to mammalian subjects (e.g., MUC1+/ERα+/− cancer patients) alone or in conjunction with other drugs and/or radiotherapy, in particular anti-ERα therapies. The compounds can also be administered to subjects that are genetically and/or environmentally (due to, for example, physiological and/or environmental factors) susceptible to cancer, e.g., subjects with a family history of cancer (e.g., breast cancer), subjects with chronic inflammation or subject to chronic stress, or subjects that are exposed to natural or non-natural environmental carcinogenic conditions (e.g., excessive exposure to sunlight, industrial carcinogens, or tobacco smoke).

When the methods are applied to subjects with cancer, prior to administration of a compound, the cancer can optionally be tested for MUC1 expression (MUC1 protein or MUC1 mRNA expression) by methods known in the art. In this way, subjects can be identified as having a MUC1-expressing or overexpressing cancer. Such methods can be performed in vitro on cancer cells obtained from a subject. Alternatively, in vivo imaging techniques using, for example, radiolabeled antibodies specific for MUC1 can be performed. In addition, body fluids (e.g., blood or urine) from subjects with cancer can be tested for elevated levels of MUC1 protein or MUC1 protein fragments.

The dosage required depends on the choice of the route of administration; the nature of the formulation; the nature of the patient's illness; the subject's size, weight, surface area, age, and sex; other drugs being administered; and the weeks. In embodiments where the anti-ERα therapy and the MUC1 peptide are applied separately to the cell, one would generally ensure that a significant period of time did not expire between the time of each delivery, such that the therapies would still be able to exert an advantageously combined effect on the cell. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the MUC1 peptide or the anti-ERα therapy will be desired. Various combinations may be employed, where the MUC1 peptide is "A" and the anti-ERα therapy is "B," as exemplified below:

| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | | judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 5-, 6-, 8-, 10-, 20-, 50-, 100-, 150-, or more times). Encapsulation of the polypeptide in a suitable delivery vehicle (e.g., polymeric microparticles or implantable devices) may increase the efficiency of delivery, particularly for oral delivery.

D. Combination Therapies

As mentioned above, it is not unusual for ERα+ cancers to develop into tamoxifen-resistant cancers. One general approach to such problems combine cancer therapies as a way of increasing their efficacy. While such approaches can be successful, it is entirely unclear whether any two therapies will work in concert to inhibit a given type of cancer. In the context of the present invention, the inventors have shown that MUC1 peptide therapy can be used successfully in conjunction with an anti-ERα agent to render resistant cells sensitive to treatment.

To kill cells, inhibit cell growth, inhibit metastasis, inhibit angiogenesis or otherwise reverse or reduce the malignant phenotype of tumor cells, using the methods and compositions of the present invention, one would generally contact a target cell with a MUC1 peptide, and optionally an anti-ERα therapy. These therapies would be provided in a combined amount effective to kill or inhibit proliferation of the cell. This process may involve contacting the cells with the agents/therapies at the same time. This may be achieved by contacting the cell with a single composition or pharmacological formulation that includes both therapies, or by contacting the cell with two distinct compositions or formulations, at the same time, wherein one composition includes the MUC1 peptide and the anti-ERα therapy.

Alternatively, the MUC1 treatment may precede or follow the anti-ERα therapy by intervals ranging from minutes to Other combinations are contemplated. Again, to achieve cell killing, both therapies are delivered to a cell in a combined amount effective to kill the cell.

E. Additional Combinations

In conjunction with the aforementioned combination therapy, other agents or factors or therapies may be suitable for combined use. These include can include any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic" or "genotoxic agents," are intended to be of use in the combined treatment methods disclosed herein. In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition.

Various classes of chemotherapeutic agents are comtemplated for use with in combination with peptides of the present invention, for example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use include, e.g., camptothecin, actinomycin-D and mitomycin C. The invention also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with a MUC1 peptide, as described above.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin, PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include Adriamycin, also known as Doxorubicin, Etoposide, Verapamil, Podophyllotoxin, and the like. Widely used in a clinical setting for the treatment of neoplasms, these compounds are administered through bolus injections intravenously at doses ranging from 25-75 mg/m$^2$ at 21 day intervals for Doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

Epidermal growth factor receptor inhibitors, such as Iressa, mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in combination cancer therapy in accordance with the present invention.

Another possible combination therapy with the peptides claimed herein is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors affect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the local or regional delivery of MUC1 peptides to patients with cancer will be a very efficient method for treating the clinical disease. Similarly, the chemo- or radiotherapy may be directed to a particular, affected region of the subject's body. Alternatively, regional or systemic delivery of expression construct and/or the agent may be appropriate in certain circumstances, for example, where extensive metastasis has occurred.

In addition to combining MUC1 therapies with chemo- and radiotherapies, it also is contemplated that combination with immunotherapy, hormone therapy, toxin therapy and surgery. It also should be pointed out that any of the foregoing therapies may prove useful by themselves in treating cancer.

V. Examples

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell Culture. Human HER2 overexpressing BT-474 breast cancer cells (ATCC) were grown in Dulbecco's Modified Eagle's Medium (DMEM)/Ham F12 medium (1:1 ratio), 10% heat-inactivated fetal bovine serum (HI-FBS), 100 µg/ml streptomycin, 100 units/ml penicillin and 2 mM L-glutamine. BT-474 cells were infected with lentiviral vector expressing a MUC1 shRNA (Sigma) or a scrambled control shRNA (CshRNA; Sigma). Human MCF-7 breast cancer and 293T renal cells (ATCC) were maintained in DMEM, 10% HI-FBS, antibiotics and L-glutamine. MCF-7 cells were transfected to stably express a control pHR-CMV-GFP vector or one expressing MUC1-C. For certain experiments performed in the absence of estrogen stimulation, cells were grown in phenol red-free Iscove's Modified Eagle's Medium (IMEM), 10% charcoal-stripped serum (CSS), antibiotics and L-glutamine. Cells were treated with tamoxifen (TAM; Sigma-Aldrich) or 4-hydroxytamoxifen (OHTAM; Sigma-Aldrich) dissolved in DMSO and, as a control, with a corresponding dilution of DMSO. The cells were also treated with the MUC1-C inhibitor GO-203 (Genus Oncology) (Raina et al., 2011).

Immunoblot analysis. Cell lysates were analyzed by immunoblotting with anti-MUC1-C (Panchamoorthy et al., 2011), anti-ERα (Santa Cruz Biotechnology), anti-p-HER2, anti-HER2 (Cell Signaling Technology), anti-p-AKT (Cell Signaling Technology), anti-AKT (Santa Cruz Biotechnology) or anti-β-actin as described (Raina et al., 2011 and Wei et al., 2006) Immune complexes were detected with horseradish peroxidase-conjugated secondary antibodies and enhanced chemiluminescence (GE Healthcare).

Colony formation assays. Cells were seeded in 6-well plates for 24 h and then left untreated or treated with inhibitor. After 7-14 d, the cells were washed and stained with 0.5% crystal violet in 25% methanol. Colonies >30 cells were counted in triplicate wells.

Chromatin immunoprecipitation (ChIP) assays. Soluble chromatin was prepared as described (16) and precipitated with anti-ERα (2 μg; Thermo Scientific) or a control non-immune IgG. For re-ChIP assays, complexes from the initial ChIP were eluted and reprecipitated with anti-MUC1-C as described (16). For PCR, 2 μl from a 50 μl DNA sample was used with the Rab31 promoter primers (16) and 25-35 cycles of amplification. Fold enrichment was calculated as described (17).

Promoter-reporter assays. Control pGL3 or pRab31-Luc constructs (Jin et al., 2012) were transfected into cells with the Renilla plasmid in the presence of Superfect (Qiagen). Luciferase activity was measured using the Promega Dual Glo kit as described (Jin et al., 2012).

qRT-PCR. Total RNA was isolated from cells using an RNeasy Mini kit (Qiagen). cDNAs were synthesized from RNA using the first-strand cDNA synthesis kit (Invitrogen) as described (Jin et al., 2012). The SYBR green qPCR assay kit (Applied Biosystems) was used with 5 μl of 20-fold diluted cDNA. The samples were amplified with the ABI Prism 7300 machine (Applied Biosystems). Rab31 and GAPDH primers used for qRT-PCR are listed in Table 1.

TABLE 1

Primers used for qRT-PCR of Rab31

| | | |
|---|---|---|
| Rab31 | Fwd: | 5'-TCAGCTGCAGCTGTTATCGT-3' |
| Rab31 | Rev: | 5'-CTGGACCATGTTCTTTCAGC-3' |
| GAPDH | Fwd: | 5'-CCATGGAGAAGGCTGGGG-3' |
| GAPDH | Rev: | 5'-CAAAGTTGTCATGGATGACC-3' |

Example 2

Results

Silencing MUC1-C confers sensitivity of BT-474 cells to tamoxifen treatment. BT-474 breast cancer cells overexpress HER2, are ER positive and are resistant to tamoxifen (Chung et al., 2002 and Ross-Innes et al., 2012). Immunoblot analysis further demonstrated that BT-474 cells express MUC1-C (FIG. 1A, left). To determine whether MUC1-C plays a role in tamoxifen resistance, the inventors transduced cells with a lentiviral vector expressing a control scrambled shRNA (CshRNA) or one expressing a MUC1 shRNA (FIG. 1A, left). Compared to wild-type (WT) BT-474 cells and those stably expressing the CshRNA, there was downregulation of MUC1-C in the cells expressing the MUC1 shRNA (FIG. 1A, left). As a control, the partial silencing of MUC1-C had little if any effect on ERα levels (FIG. 1A, left). MUC1 interacts with HER2 and promotes HER2-mediated signaling (Li et al., 2003c and Ren et al., 2006). In this context, partial silencing of MUC1-C in BT-474 cells was associated with downregulation of p-HER2 and no detectable effect on HER2 levels (FIG. 1A, right). With regard to tamoxifen resistance, growth of BT-474 and BT-474/CshRNA cells was unaffected by the addition of tamoxifen as compared to that obtained with untreated cells (FIG. 1B). By contrast, proliferation of BT-474/MUC1shRNA cells was clearly inhibited by tamoxifen treatment (FIG. 1B). In addition, the BT-474/MUC1 shRNA cells exhibited a marked loss of viability in response to tamoxifen as compared to that obtained for BT-474/CshRNA cells (FIG. 1C, left). Similar results were obtained when the cells were treated with OHTAM (FIG. 1C, right). Plating efficiency of BT-474/MUC1 shRNA cells was also significantly decreased compared to BT-474/CshRNA cells (FIG. 1D, left and right). As expected, tamoxifen had little if any effect on the ability of BT-474/CshRNA to form colonies (FIG. 1E, left). Notably, however, tamoxifen treatment was associated with a marked decrease in BT-474/MUC1 shRNA cell colony formation (FIG. 1E, right). These findings indicate that MUC1-C contributes to tamoxifen resistance in BT-474 cells.

Overexpression of the MUC1-C subunit confers resistance of MCF-7 cells to tamoxifen. In contrast to BT-474 cells, MCF-7 breast cancer cells are ER+ and sensitive to tamoxifen. To extend the analysis of MUC1-C involvement in tamoxifen resistance, MCF-7 cells were stably transfected with a control vector or one expressing MUC1-C (FIG. 2A). Overexpression of MUC1-C resulted in a modest increase in ERα levels (FIG. 2A). In addition and consistent with the reported effects of MUC1-C on upregulation of the PI3K→AKT pathway (Raina et al., 2004 and Raina et al., 2011), overexpression of MUC1-C in MCF-7 cells was associated with a marked induction of p-AKT activation (FIG. 2A). Growth of MCF-7 and MCF-7/vector cells was inhibited by tamoxifen (FIG. 2B). Significantly, however, tamoxifen treatment had little effect on proliferation of MCF-7/MUC1-C cells (FIG. 2B). The MCF-7/MUC1-C cells were also less sensitive to tamoxifen- and OHTAM-induced loss of viability as compared to MCF-7/vector cells (FIG. 2C, left and right). Plating efficiency of MCF-7/MUC1-C cells was substantially increased compared to MCF-7/vector cells (FIG. 2D, left and right). Moreover, tamoxifen was effective in decreasing formation of MCF-7/vector cell colonies (FIG. 2E, left), but not clonogenic survival of MCF-7/MUC1-C cells (FIG. 2E, right). These findings indicate that overexpression of MUC1-C in MCF-7 cells confers activation of AKT and tamoxifen resistance.

MUC1-C confers MCF-7 cell growth in the absence of estrogen. Growth of MCF-7 cells is dependent on estrogen (Miller et al., 2010). The demonstration that MUC1-C confers resistance to tamoxifen prompted studies to determine whether MCF-7/MUC1-C cells are also estrogen-independent. Culture of MCF-7/vector cells in estrogen-depleted IMEM/CSS medium was associated with inhibition of growth (FIG. 3A). Strikingly, however, proliferation of MCF-7/MUC1-C cells was readily apparent in the setting of estrogen depletion (FIG. 3A). Loss of MCF-7/vector cell viability in the absence of estrogen stimulation was also abrogated by MUC1-C overexpression (FIG. 3B). In addition, the plating efficiency of MCF-7/MUC1-C cells in IMEM/CSS medium was substantially greater than that found for MCF-7/vector cells (FIG. 3C, left and right). These findings demonstrate that overexpression of MUC1-C in MCF-7 cells confers estrogen independence.

MUC1-C abrogates effects of tamoxifen on ERα-mediated gene transcription. To study the effects of MUC1-C on the response of an estrogen-responsive gene to tamoxifen, the inventors first examined ERα and MUC1-C occupancy of the Rab31 promoter by ChIP analysis (16). In this context, recent work showed that MUC1-C forms a complex with ERα on the Rab31 promoter and activates Rab31 gene transcription in an estrogen-dependent manner (Jin et al., 2012). Tamoxifen treatment of MCF-7/vector and MCF-7/

MUC1-C cells had little if any effect on ERα levels (FIG. 7). However, in MCF-7/vector cells, tamoxifen treatment was associated with decreased ERα occupancy of the Rab31 promoter (FIG. 4A, left). By contrast, tamoxifen treatment of MCF-7/MUC1-C cells had no apparent effect on ERα occupancy (FIG. 4A, right). In re-ChIP studies, occupancy of the Rab31 promoter by ERα and MUC1-C was also decreased by tamoxifen in MCF-7/vector (FIG. 4B, left), but not MCF-7/MUC1-C, cells (FIG. 4B, right). The CREB binding protein (CBP) is a histone acetyltransferase that is recruited to ligand-activated, DNA-bound ERα, and enhances ERα-mediated gene transcription (Acevedo and Kraus, 2003 and Jaber et al., 2004). Recruitment of CBP to the Rab31 promoter in MCF-7/vector cells was decreased by tamoxifen treatment (FIG. 4C, left); however, tamoxifen had no significant effect on CBP occupancy in MCF-7/MUC1-C cells (FIG. 4C, right). To extend these results, the inventors studied activation of the Rab31 promoter using a Rab31 promoter-luciferase reporter construct. Tamoxifen treatment was associated with a decrease in Rab31 promoter activity in MCF-7/vector, but not in MCF-7/MUC1-C, cells (FIG. 4D). In concert with these results, tamoxifen-induced downregulation of Rab31 mRNA levels as observed in MCF-7/vector cells was attenuated in MCF-7/MUC1-C cells (FIG. 4E, left and right). Moreover, Rab31 protein was decreased by tamoxifen treatment of MCF-7/vector, but not MCF-7/MUC1-C, cells (FIG. 4F). These findings demonstrate that MUC1-C blocks the inhibitory effects of tamoxifen on ERα occupancy, CBP recruitment and Rab31 promoter activity.

Figure 8:
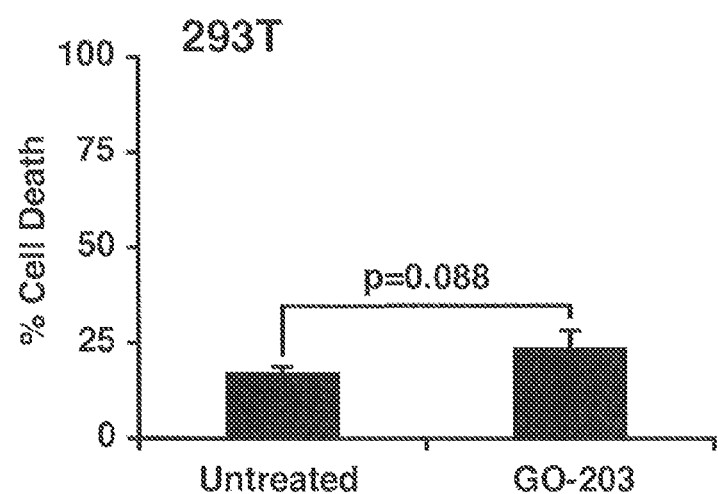
FIG. 8. 293T cells were left untreated or treated with GO-203 each day for 4 days. The results (mean±SD of three replicates) are expressed as the percentage of cell death as determined by trypan blue staining on day 4.

Tamoxifen-resistant breast cancer cells are sensitive to MUC1-C inhibition. The finding that MUC1-C confers tamoxifen resistance invoked the possibility that MUC1-C inhibitors could be effective in tamoxifen-resistant cells. Accordingly, the inventors treated BT-474 cells with the MUC1-C inhibitor GO-203, a cell-penetrating D-amino acid peptide ([R]$_9$-CQCRRKN) (Raina et al., 2011). GO-203 treatment of BT-474 cells was associated with marked downregulation of p-HER2 and p-AKT (FIG. 5A). In addition, treatment with GO-203 was associated with inhibition of growth (FIG. 5B) and loss of clonogenic survival (FIG. 5C). By contrast, GO-203 had little if any effect on survival of MUC1-negative 293T cells (FIG. 8). GO-203 treatment of MCF-7/MUC1-C cells also inhibited AKT activation (FIG. 5D), growth (FIG. 5E) and colony formation (FIG. 5F). Moreover, inhibition of MUC1-C with GO-203 decreased recruitment of ERα and CBP to the Rab31 promoter (FIG. 5G). These results indicate that tamoxifen-resistant BT-474 and MCF-7/MUC1-C cells are dependent on MUC1-C function for their growth and survival.

Synergy between GO-203 and tamoxifen in tamoxifen-resistant breast cancer cells. The above findings demonstrate that silencing MUC1-C in BT-474 cells results in tamoxifen sensitivity. To further substantiate that MUC1-C confers tamoxifen resistance, the inventors silenced MUC1-C in MCF-7/MUC1-C cells (FIG. 6A). Notably, the MCF-7/MUC1-C/MUC1shRNA cells regained sensitivity to tamoxifen treatment (FIG. 6B). These results suggested that targeting MUC1-C in tamoxifen-resistant cells could potentiate tamoxifen treatment. To address this line of reasoning, the inventors used the Chou-Talalay method for evaluating drug combinations (Chou, 1984; 2010). For the tamoxifen-resistant BT-474/CshRNA cells, the inventors had to select a concentration of tamoxifen for the combination studies. Accordingly, the inventors used the IC$_{50}$ (16.6 µM) obtained for the tamoxifen-sensitive BT-474/MUC1shRNA cells, based on the reasoning that targeting MUC1-C in BT-474 cells reverses tamoxifen resistance. Using the half-maximal inhibitory concentration for GO-203 (3.9 µM), GO-203 and tamoxifen were tested alone for their effects on BT-474/CshRNA cell growth at ⅛×, ¼×, ½×, 1×, 2× and 4× the IC50 values. GO-203 and tamoxifen were also tested at equipotent concentrations at the same ratios in combination. Isobologram analysis at the ED50, ED75 and ED90 values demonstrated synergy for the GO-203/tamoxifen combination (FIG. 6C) with combination indices (CIs) of less than 1 (ED$_{50}$=0.81; ED$_{75}$=0.56, ED$_{90}$=0.43). A synergistic interaction between GO-203 and tamoxifen with CIs of <1 (ED$_{50}$=0.79; ED$_{75}$=0.57; ED$_{90}$=0.50) was also observed in the tamoxifen-sensitive BT-474/MUC1shRNA cells (FIG. 9A). In assessing the combined effects of GO-203 and tamoxifen against MCF-7/vector cells, the inventors found that the activity of GO-203 and tamoxifen is synergistic at the ED$_{50}$ (CI=0.69) and ED$_{75}$ (CI=0.88), and additive at the ED$_{90}$ (CI=1.12) (FIG. 9B). To assess these drug interactions in the tamoxifen-resistant MCF-7/MUC1-C cells, the inventors used the half-maximal inhibitory concentration identified for tamoxifen in the treatment of MCF-7/vector cells, based on the demonstration that targeting MUC1-C in MCF-7/MUC1-C cells reverses tamoxifen resistance. Under these experimental conditions, a synergistic interaction between GO-203 and tamoxifen was observed for MCF-7/MUC1-C cells with CIs of <1 (ED$_{50}$=0.65; ED$_{75}$=0.56; ED$_{90}$=0.49) (FIG. 6D). These results and those obtained with BT-474 cells demonstrate that GO-203 and tamoxifen are synergistic in the treatment of both tamoxifen-sensitive and -resistant cells.

Example 3

Discussion

The overexpression of HER2 in breast cancers has been linked to tamoxifen resistance (De Laurentis et al., 2005). The present studies provide evidence that the MUC1-C oncoprotein promotes resistance to tamoxifen in the HER2 overexpressing BT-474 breast cancer cell model. Previous work had shown that MUC1-C forms a complex with HER2 and contributes to Heregulin-induced downstream signals (Ren et al., 2006; Yin and Kufe, 2003). In concert with those findings, silencing MUC1-C in BT-474 cells was associated with downregulation of p-HER2 levels. Moreover, silencing MUC1-C and thereby suppressing HER2 activation reversed the resistance of BT-474 cells to tamoxifen, consistent with cross-talk between HER2 signaling and the ER pathway. In further support of a role for MUC1-C in resistance of HER2-overexpressing BT-474 cells to tamoxifen, the inventors found that treatment with the MUC1-C inhibitor, GO-203, suppresses HER2 activation and confers sensitivity to tamoxifen-induced inhibition of growth and colony formation. GO-203 disrupts MUC1-C homodimerization and blocks the interaction of MUC1-C with HER2 at the cell membrane (Kufe, 2012). In this way, silencing MUC1-C or blocking its function with an inhibitor results in HER2 downregulation and reversal of tamoxifen resistance. In addition to HER2, activation of EGFR and IGF1-R can confer tamoxifen resistance (Musgrove et al., 2009). Moreover, like EGFR and IGF1-R, HER2 activates downstream signals that confer phosphorylation of ER and can result in tamoxifen-mediated activation or ligand-independence (Osborne et al., 2011, Arpino et al., 2008 and Shou et al., 2004). Activation of pathways downstream to these RTKs can also contribute to tamoxifen resistance (Musgrove 2009). For example, signaling by the PI3K→AKT→mTOR pathway as a consequence of HER2 overexpression or loss of PTEN can regulate responsiveness to tamoxifen (Aprino et al., 2008, Faridi et al., 2003, deGraffenried et al., 2013, deGraffenried et al., 2004, Riggins et al., 2007). However, the precise mechanisms that confer tamoxifen resistance have not been fully defined and may involve activation of mitogenic and anti-apoptotic pathways (Osborne et al., 2011 and Musgrove et al., 2009).

These studies further demonstrate that overexpression of MUC1-C in MCF-7 cells induces tamoxifen resistance. MCF-7 cells constitutively express MUC1; however, MUC1-C levels are not sufficient to activate the PI3K→AKT pathway. Indeed, as has been shown in other cell types (Raina et al., 2004 and Raina et al., 2011), overexpression of MUC1-C in MCF-7 cells was associated with marked upregulation of AKT activation. In this way, MUC1-C interacts directly with PI3K through binding of PI3K SH2 domains to a consensus pYHPM motif in the MUC1-C cytoplasmic domain and activates the PI3K→AKT pathway (Raina et al., 2004, Raina et al., 2011 and, Jin et al., 2012). The PI3K pathway is hyperactivated in response to the development of resistance to estrogen deprivation (Miller et al., 2010). In addition, activation of PI3K signaling has been linked to antiestrogen resistance in breast cancer cells (Miller et al., 2011). In concert with these findings, MCF-7 cells that overexpress MUC1-C were found to be resistant to estrogen deprivation. Moreover, MUC1-C overexpression was sufficient to confer resistance to tamoxifen-induced loss of proliferation and clonogenic survival. Notably, treatment of MCF-7/MUC1-C cells with the MUC1-C inhibitor GO-203 was associated with a block in AKT activation, consistent with MUC1-C function in activating the PI3K→AKT pathway. GO-203 treatment was also associated with reversal of MUC1-C-induced tamoxifen resistance. These findings and those obtained in the BT-474 model of HER2 overexpression indicate that MUC1-C is sufficient to confer tamoxifen resistance by contributing, at least in part, to signaling pathways, such as AKT, that have been linked to ER activity.

Previous findings have demonstrated that MUC1-C binds directly to the ERα DNA binding domain and associates with ERα on estrogen-responsive promoters (Wei et al., 2006). MUC1-C was also found to enhance ERα promoter occupancy and increase recruitment of coactivators (Wei et al., 2006). In the present work, the inventors studied the effects of MUC1-C on ERα occupancy in the response to tamoxifen treatment. MUC1-C forms a complex with ERα on the ERα-responsive Rab31 promoter and activates Rab31 gene transcription in an estrogen-dependent manner (Jin et al., 2012). Treatment with tamoxifen was associated with a decrease in ERα occupancy on the Rab31 promoter and this response was blocked by overexpression of MUC1-C. Tamoxifen competes with estrogen for binding to ERα and induces changes in ERα conformation that block recruitment of coactivators (Brzozowski et al., 1997 and Shang et al., 2000). In this context, tamoxifen treatment was associated with decreases in recruitment of CBP to the Rab31 promoter and this response was also attenuated by a MUC1-C. MUC1-C contributes to the availability of ERα/E2 complexes for occupancy of estrogen-responsive elements (Wei et al., 2006). In addition, through a direct interaction with ERα and increasing ERα/E2 complexes, MUC1-C attenuates the competitive effects of tamoxifen on estrogen binding (Wei et al., 2006). These findings further indicated that overexpression of MUC1-C promotes the transcription of ER-dependent genes and thereby survival of ER+ breast cancer cells (Wei et al., 2006). Thus, the available evidence indicates that, in concert with MUC1-C-induced regulation of the HER2 and AKT pathways, binding of MUC1-C to ERα may also contribute to attenuating the effects of tamoxifen.

The MUC1-C cytoplasmic domain contains a CQC motif that is necessary for its dimerization and nuclear localization (Leng et al., 2007). Accordingly, cell penetrating peptides and small molecules have been developed to block the CQC dimerization motif (Raina et al. 2009 and Zhou et al., 2011). In this way, treatment with MUC1-C inhibitors abrogates the formation of MUC1-C homodimers and thereby MUC1-C function in breast cancer cells (Raina et al., 2009 and Raina et al., 2012). The present work demonstrates that treatment of tamoxifen-resistant BT-474 cells with the MUC1-C inhibitor, GO-203, is associated with inhibition of growth and loss of clonogenicity, supporting a lack of cross-resistance to targeting MUC1-C. MCF-7 cells with induced resistance to tamoxifen as a result of overexpressing MUC1-C were also sensitive to GO-203 treatment. These findings invoked the possibility that MUC1-C-induced tamoxifen resistance might be reversed by targeting MUC1-C. Tamoxifen-resistant cells were therefore treated with GO-203 in combination with tamoxifen. The demonstration that GO-203 and tamoxifen are highly synergistic against tamoxifen-resistant cells provided further support that MUC1-C is of importance to tamoxifen resistance. By extension, GO-203 and tamoxifen were also found to be synergistic in the treatment of tamoxifen-sensitive cells. These results lend support to the concept that targeting MUC1-C could be effective in the treatment of patients with breast cancers that develop resistance to tamoxifen. A Phase I trial of GO-203 is presently underway for patients with refractory solid tumors to identify a maximum tolerated dose for Phase II studies. Based on the present findings, this agent may be a candidate for evaluation in the treatment of tamoxifen-resistant breast cancers.

* * *

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. References

The following references, to the extent that they provide exemplary procedural or other details supplementary to those set forth herein, are specifically incorporated herein by reference:

U.S. Pat. No. 5,440,013
U.S. Pat. No. 5,446,128
U.S. Pat. No. 5,475,085
U.S. Pat. No. 5,618,914
U.S. Pat. No. 5,670,155
U.S. Pat. No. 5,672,681
U.S. Pat. No. 5,674,976
U.S. Pat. No. 5,710,245

U.S. Pat. No. 5,840,833
U.S. Pat. No. 5,859,184
U.S. Pat. No. 5,889,155
U.S. Pat. No. 5,929,237
U.S. Pat. No. 6,261,569
U.S. Pat. No. 7,183,059
U.S. Pat. No. 7,192,713
Abe and Kufe, *Cancer Res.,* 49(11):2834-2839, 1989.
Arpino et al., *Endocr Rev.,* 29:217-33, 2008.
Baldus et al., *Clin. Cancer Res.,* 10(8):2790-2796, 2004.
Bodanszky et al., *J. Antibiot.,* 29(5):549-53, 1976.
Brzozowski, et al., *Nature,* 389:753-8, 1997.
Chou, et al., *Adv Enzyme Regul,* 22:27-55, 1984.
Chou, et al., *Cancer Res.,* 70:440-6, 2010.
Chung et al., *Int J Cancer* 97:306-12; 2002.
deGraffenried, et al., *Ann Oncol.,* 14:1051-6, 2013.
deGraffenried et al., *Clin Cancer Res.,* 10:8059-67, 2004.
De Laurentiis et al., *Clin Cancer Res.,* 11:4741-8, 2005.
Ellis et al., *J Clin Oncol.,* 24:3019-25, 2006.
Faridi, et al., *Clin Cancer Res.,* 9:2933-9, 2003.
Fischer, *Med. Res. Rev.,* 27(6):755-796, 2007.
Gendler et al., *J. Biol. Chem.,* 263:12820-12823, 1988.
Gutierrez et al., *J Clin Oncol.,* 23:2469-76, 2005.
Hodel et al., *Mol. Cell,* 10(2):347-58, 2002.
Huang et al., *Cancer Biol Ther.,* 2:702-706, 2003.
Huang et al., *Cancer Res.,* 65:10413-10422, 2005.
Jaber et al., *J Mol Endocrinol,* 32:307-23, 2004.
Jin *Oncogene,* Jun. 11, 2012.
Jin, et al., *PLoS One* 7:e39432, 2012.
Johnson et al., In: *Biotechnology And Pharmacy,* Pezzuto et al. (Eds.), Chapman and Hall, NY, 1993.
Kau et al., *Nat. Rev. Cancer,* 4(2):106-17, 2004.
Kinlough et al., *J. Biol. Chem.,* 279(51):53071-53077, 2004.
Kufe et al., *Hybridoma,* 3:223-232, 1984.
Kufe *Nature Reviews Cancer,* 9:874-85, 2009.
Kufe *Oncogene,* 2012.
Leng et al., *J Biol Chem.,* 282:19321-30, 2007.
Levitan et al., *J. Biol. Chem.,* 280:33374-33386, 2005.
Li et al., *Cancer Biol. Ther.,* 2:187-193, 2003b.
Li et al., *J. Biol. Chem.,* 276:35239-35242, 2001.
Li et al., *J. Biol. Chem.,* 276:6061-6064, 2001.
Li et al., *Mol. Cancer Res.,* 1:765-775, 2003c.
Li et al., *Mol. Cell Biol.,* 18:7216-7224, 1998.
Li et al., *Oncogene,* 22:6107-6110, 2003a.
Ligtenberg et al., *J. Biol. Chem.,* 267, 6171-6177, 1992.
Macao, *Nat. Struct. Mol. Biol.,* 13, 71-76, 2006.
Merlo et al., *Cancer Res.,* 49, 6966-6971, 1989.
Merrifield, *J. Am. Chem. Soc.,* 85:2149-2154, 1963.
Miller et al., *J Clin Invest.,* 120:2406-13, 2010.
Miller et al., *Cancer Discov.,* 1:338-51, 2011.
Miller et al., *J Clin Oncol.,* 29:4452-61, 2011.
Musgrove et al., *Nat Rev Cancer* 9:631-43, 2009.
Osborne et al., *Annu Rev Med.,* 62:233-47, 2011.
Panchamoorthy et al., *Hybridoma* 30:531-5, 2011.
Peptide Synthesis, 1985
Percipalle et al., *J. Mol. Biol.,* (4):722-32, 1997.
Perey et al., *Cancer Res.,* 52(22):6365-6370, 1992.
Pitroda et al., *Proc Natl Acad Sci USA,* 106:5837-41, 2009.
Raina et al., *J Biol Chem.,* 279:20607-12, 2004.
Raina et al., *EMBO J.,* 25:3774-3783, 2006.
Raina, et al., *Cancer Res.,* 69:5133-41, 2009.
Raina et al., *Mol Cancer Therapeutics,* 10:806-16, 2011.
Raina, et al., *Int J Oncol.,* 40:1643-9, 2012.
Remington's Pharmaceutical Sciences, 15$^{th}$ Ed., 3:624-652, 1990
Remington's Pharmaceutical Sciences, 15$^{th}$ Ed., 1035-1038 and 1570-1580, 1990.
Ren et al., *J. Biol. Chem.,* 277:17616-17622, 2002.
Ren et al., *Cancer Cell,* 5:163-175, 2004.
Ren et al., *Oncogene,* 25:20-31, 2006.
Riggins et al., *Cancer Lett.,* 256:1-24, 2007.
Ross-Innes, et al., *Nature;* 481:389-93, 2012.
Ryan and Wente, *Curr. Opin. Cell Biol.,* 12(3):361-71, 2000.
Schafmeister et al., *J. Am. Chem. Soc.,* 122(24): p. 5891-5892, 2000.
Schroeder et al., *Oncogene,* 23:5739-5747, 2004.
Shang, et al., *Cell,* 103:843-52, 2000.
Shou, et al., *J Natl Cancer Inst.,* 96:926-35, 2004.
Siddiqui et al., *Proc. Natl. Acad. Sci. USA,* 85:2320-2323, 1988.
Solid Phase Peptide Synthelia, 1984
Suh and Gumbiner, *Exp. Cell Res.,* 290(2):447-56, 2003.
Vermeer et al., *Nature,* 422(6929):322-6, 2003.
Weber, *Advances Protein Chem.,* 41:1-36, 1991.
Wei et al., *Cancer Cell,* 7:167-178, 2005.
Wei et al., *Mol Cell,* 21:295-305, 2006.
Weis, *Cell,* 112(4):441-51, 2003.
Wen et al., *J. Biol. Chem.,* 278:38029-38039, 2003.
Yamamoto et al., *J. Biol. Chem.,* 272:12492-12494, 1997.
Yin et al., *J. Biol. Chem.,* 279:45721-45727, 2004.
Yin et al., *J. Biol. Chem.,* 282:257-266, 2007.
Yin and Kufe, *J. Biol. Chem.,* 278:35458-35464, 2003a.
Yin and Kufe, *J. Biol. Chem.,* 278:35458-35464, 2003b.
Zhou, et al., *Mol Pharm.,* 79:886-93, 2011.

---

The invention claimed is:

1. A method of inhibiting a MUC1-positive/ERα-positive tumor cell in a subject comprising administering to said subject a MUC1 peptide of at least 4 consecutive MUC1 residues and no more than 20 consecutive MUC1 residues and comprising the sequence CQC (SEQ ID NO: 4), wherein the amino-terminal cysteine of CQC is covered on its NH$_2$-terminus by at least one amino acid residue that need not correspond to the native MUC-1 transmembrane sequence, wherein said tumor cell exhibits primary resistance to tamoxifen.

2. The method of claim 1, wherein said peptide comprises at least 5, 6, 7 or 8 consecutive MUC1 residues.

3. The method of claim 1, wherein said peptide contains no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1.

4. The method of claim 1, wherein the tumor cell is a carcinoma cell.

5. The method of claim 4, wherein the carcinoma cell is a breast carcinoma cell.

6. The method of claim 1, wherein said peptide is fused to a cell delivery domain.

7. The method of claim 6, wherein said cell delivery domain is poly-D-R, poly-D-P or poly-D-K.

8. The method of claim 1, wherein administering comprises intravenous, intra-arterial, intra-tumoral, subcutaneous, topical or intraperitoneal administration.

9. The method of claim 1, wherein administering comprises local, regional, systemic, or continual administration.

10. The method of claim 1, wherein inhibiting comprises inducing growth arrest of said tumor cell, apoptosis of said tumor cell and/or necrosis of a tumor tissue comprising said tumor cell.

11. The method of claim 1, further comprising administering to said subject an anti-ERαtherapy.

12. The method of claim 11, wherein said anti-ERα therapy is tamoxifen.

13. The method of claim 11, wherein said anti-ERα therapy is administered prior to said peptide.

14. The method of claim 11, wherein said anti-ERα therapy is administered after said peptide.

15. The method of claim 11, wherein said anti-ERα therapy is administered at the same time as said peptide.

16. The method of claim 1, wherein said subject is a human.

17. The method of claim 1, wherein said peptide is administered at 0.1-500 mg/kg/d.

18. The method of claim 1, wherein said peptide is administered at 10-100 mg/kg/d.

19. The method of claim 1, wherein said peptide is administered daily.

20. The method of claim 19, wherein said peptide is administered daily for 7 days, 2 weeks, 3 weeks, 4 weeks, one month, 6 weeks, 8 weeks, two months, 12 weeks, or 3 months.

21. The method of claim 1, wherein said peptide is administered weekly.

22. The method of claim 21, wherein said peptide is administered weekly for 2 weeks, 3 weeks, 4 weeks, 6 weeks, 8 weeks, 10 weeks, or 12 weeks.

23. The method of claim 1, wherein said peptide comprises all L amino acids.

24. The method of claim 1, wherein said peptide comprises all D amino acids.

25. The method of claim 1, wherein said peptide comprises a mix of L and D amino acids.

26. The method of claim 1, further comprising the step of assessing the expression of MUC1 in a tumor cell of said subject prior to administering said peptide.

27. The method of claim 1, further comprising the step of assessing the expression of ERα in a tumor cell of said subject prior to administering said peptide.

28. The method of claim 1, wherein said subject has metastatic cancer.

29. The method of claim 1, wherein said subject has recurrent cancer.

30. The method of claim 1, wherein said peptide is at least 8 residues in length, and at least two non-adjacent residues form a bridge through their side chains.

31. The method of claim 30, wherein the bridge comprises a linker, chemically modified side chains, or hydrocarbon stapling.

32. The method of claim 31, wherein the linker comprises a modification that stabilizes an alpha-helical structure of said peptide.

33. The method of claim 1, wherein ERα is overexpressed as compared to a similar non-cancerous cell.

34. The method of claim 4 wherein the carcinoma cell is a prostate carcinoma cell.

35. The method of claim 11, wherein said subject has previously received an anti-ERα therapy.

36. A method of inhibiting a MUC1-positive tumor cell in a subject comprising administering to said subject a MUC1 peptide of at least 4 consecutive MUC1 residues and no more than 20 consecutive MUC1 residues and comprising the sequence CQC (SEQ ID NO: 4), wherein the amino-terminal cysteine of CQC is covered on its $NH_2$-terminus by at least one amino acid residue that need not correspond to the native MUC-1 transmembrane sequence, wherein said tumor cell exhibits resistance to tamoxifen.

* * * * *

UNITED STATES PATENT AND TRADEMARK OFFICE
CERTIFICATE OF CORRECTION

PATENT NO. : 9,572,855 B2
APPLICATION NO. : 14/774163
DATED : February 21, 2017
INVENTOR(S) : Donald W. Kufe and Surender Kharbanda Page 1 of 1

It is certified that error appears in the above-identified patent and that said Letters Patent is hereby corrected as shown below:

In the Specification

Column 1, Lines 12-15, delete the entire contents of Lines 12-15 and replace with --This invention was made with government support under grant numbers CA166480 and CA097098 awarded by The National Institutes of Health. The government has certain rights in the invention-- therefor.

In the Claims

In Claim 11, Column 49, Line 61, delete "anti-ERαtherapy" and replace with --anti-ERα therapy-- therefor.

Signed and Sealed this
Sixteenth Day of May, 2017

Michelle K. Lee
*Director of the United States Patent and Trademark Office*

SEQUENCE LISTING

<160> NUMBER OF SEQ ID NOS: 48

<210> SEQ ID NO 1
<211> LENGTH: 159
<212> TYPE: PRT
<213> ORGANISM: Homo sapiens

<400> SEQUENCE: 1

Gly Ser Val Val Val Gln Leu Thr Leu Ala Phe Arg Glu Gly Thr Ile
1               5                   10                  15

Asn Val His Asp Val Glu Thr Gln Phe Asn Gln Tyr Lys Thr Glu Ala
            20                  25                  30

Ala Ser Arg Tyr Asn Leu Thr Ile Ser Asp Val Ser Val Ser Asp Val
        35                  40                  45

```
Pro Phe Pro Phe Ser Ala Gln Ser Gly Ala Gly Val Pro Gly Trp Gly
        50                  55                  60

Ile Ala Leu Leu Val Leu Val Cys Val Leu Val Ala Leu Ala Ile Val
 65                  70                  75                  80

Tyr Leu Ile Ala Leu Ala Val Cys Gln Cys Arg Arg Lys Asn Tyr Gly
                 85                  90                  95

Gln Leu Asp Ile Phe Pro Ala Arg Asp Thr Tyr His Pro Met Ser Glu
            100                 105                 110

Tyr Pro Thr Tyr His Thr His Gly Arg Tyr Val Pro Pro Ser Ser Thr
            115                 120                 125

Asp Arg Ser Pro Tyr Glu Lys Val Ser Ala Gly Asn Gly Gly Ser Ser
130                 135                 140

Leu Ser Tyr Thr Asn Pro Ala Val Ala Ala Thr Ser Ala Asn Leu
145                 150                 155

<210> SEQ ID NO 2
<211> LENGTH: 72
<212> TYPE: PRT
<213> ORGANISM: Homo sapiens

<400> SEQUENCE: 2

Cys Gln Cys Arg Arg Lys Asn Tyr Gly Gln Leu Asp Ile Phe Pro Ala
 1               5                  10                  15

Arg Asp Thr Tyr His Pro Met Ser Glu Tyr Pro Thr Tyr His Thr His
             20                  25                  30

Gly Arg Tyr Val Pro Pro Ser Ser Thr Asp Arg Ser Pro Tyr Glu Lys
         35                  40                  45

Val Ser Ala Gly Asn Gly Gly Ser Ser Leu Ser Tyr Thr Asn Pro Ala
 50                  55                  60

Val Ala Ala Thr Ser Ala Asn Leu
 65                  70

<210> SEQ ID NO 3
<211> LENGTH: 15
<212> TYPE: PRT
<213> ORGANISM: Homo sapiens

<400> SEQUENCE: 3

Cys Gln Cys Arg Arg Lys Asn Tyr Gly Gln Leu Asp Ile Phe Pro
 1               5                  10                  15

<210> SEQ ID NO 4
<211> LENGTH: 3
<212> TYPE: PRT
<213> ORGANISM: Artificial Sequence
<220> FEATURE:
<223> OTHER INFORMATION: Synthetic peptide

<400> SEQUENCE: 4

Cys Gln Cys
 1

<210> SEQ ID NO 5
<211> LENGTH: 34
<212> TYPE: PRT
<213> ORGANISM: Artificial Sequence
<220> FEATURE:
<223> OTHER INFORMATION: Synthetic peptide

<400> SEQUENCE: 5

Gln Ala Ala Thr Ala Thr Arg Gly Arg Ser Ala Ala Ser Arg Pro Thr
```

```
1               5                   10                  15
Glu Arg Pro Arg Ala Pro Ala Arg Ser Ala Ser Arg Pro Arg Pro
            20                  25                  30
Val Glu

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Arg Arg Met Lys Trp Lys Lys
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Arg Arg Trp Arg Arg Trp Trp Arg Arg Trp Trp Arg Arg Trp Arg Arg
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: Synthetic peptide

<400> SEQUENCE: 9

Arg Gly Gly Arg Leu Ser Tyr Ser Arg Arg Phe Ser Thr Ser Thr
1               5                   10                  15

Gly Arg

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Tyr Gly Arg Lys Lys Arg Arg Gln Arg Arg
1               5                   10

<210> SEQ ID NO 11
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 11

Arg Lys Lys Arg Arg Gln Arg Arg
1               5

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

Tyr Ala Arg Ala Ala Ala Arg Gln Ala Arg Ala
1               5                  10

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Arg Arg Arg Arg Arg Arg Arg Arg
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide

<400> SEQUENCE: 14

Lys Lys Lys Lys Lys Lys Lys Lys
1               5

<210> SEQ ID NO 15
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 15

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 16
<211> LENGTH: 18
<212> TYPE: PRT
<213> ORGANISM: Artificial Sequence
<220> FEATURE:
<223> OTHER INFORMATION: Synthetic peptide

<400> SEQUENCE: 16

Leu Leu Ile Leu Leu Arg Arg Arg Ile Arg Lys Gln Ala Asn Ala His
1               5                   10                  15
```

Ser Lys

<210> SEQ ID NO 17
<211> LENGTH: 16
<212> TYPE: PRT
<213> ORGANISM: Artificial Sequence
<220> FEATURE:
<223> OTHER INFORMATION: Synthetic peptide

<400> SEQUENCE: 17

```
Ser Arg Arg His His Cys Arg Ser Lys Ala Lys Arg Ser Arg His His
1               5                   10                  15
```

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide

<400> SEQUENCE: 18

```
Asn Arg Ala Arg Arg Asn Arg Arg Arg Val Arg
1               5                   10
```

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

```
Arg Gln Leu Arg Ile Ala Gly Arg Arg Leu Arg Gly Arg Ser Arg
1               5                   10                  15
```

<210> SEQ ID NO 20
<211> LENGTH: 13
<212> TYPE: PRT
<213> ORGANISM: Artificial Sequence
<220> FEATURE:
<223> OTHER INFORMATION: Synthetic peptide

<400> SEQUENCE: 20

```
Lys Leu Ile Lys Gly Arg Thr Pro Ile Lys Phe Gly Lys
1               5                   10
```

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

```
Arg Arg Ile Pro Asn Arg Arg Pro Arg Arg
1               5                   10
```

<210> SEQ ID NO 22
<211> LENGTH: 17
<212> TYPE: PRT
<213> ORGANISM: Artificial Sequence
<220> FEATURE:
<223> OTHER INFORMATION: Synthetic peptide

<400> SEQUENCE: 22

```
Lys Leu Ala Leu Lys Leu Ala Leu Lys Ala Leu Lys Ala Ala Leu Lys
```

```
1               5                   10                  15

Leu

<210> SEQ ID NO 23
<211> LENGTH: 14
<212> TYPE: PRT
<213> ORGANISM: Artificial Sequence
<220> FEATURE:
<223> OTHER INFORMATION: Synthetic peptide

<400> SEQUENCE: 23

Lys Leu Ala Lys Leu Ala Lys Lys Leu Ala Lys Leu Ala Lys
1               5                   10

<210> SEQ ID NO 24
<211> LENGTH: 27
<212> TYPE: PRT
<213> ORGANISM: Artificial Sequence
<220> FEATURE:
<223> OTHER INFORMATION: Synthetic peptide

<400> SEQUENCE: 24

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 25
<211> LENGTH: 21
<212> TYPE: PRT
<213> ORGANISM: Artificial Sequence
<220> FEATURE:
<223> OTHER INFORMATION: Synthetic peptide

<400> SEQUENCE: 25

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 26
<211> LENGTH: 23
<212> TYPE: PRT
<213> ORGANISM: Artificial Sequence
<220> FEATURE:
<223> OTHER INFORMATION: Synthetic peptide

<400> SEQUENCE: 26

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 27
<211> LENGTH: 23
<212> TYPE: PRT
<213> ORGANISM: Artificial Sequence
<220> FEATURE:
<223> OTHER INFORMATION: Synthetic peptide

<400> SEQUENCE: 27

Met Gly Leu Gly Leu His Leu Leu Val Leu Ala Ala Ala Leu Gln Gly
1               5                   10                  15

Ala Lys Ser Lys Arg Lys Val
```

<210> SEQ ID NO 28
<211> LENGTH: 26
<212> TYPE: PRT
<213> ORGANISM: Artificial Sequence
<220> FEATURE:
<223> OTHER INFORMATION: Synthetic peptide

<400> SEQUENCE: 28

Ala Ala Val Ala Leu Leu Pro Ala Val Leu Leu Ala Leu Leu Ala Pro
1               5                   10                  15
Ala Ala Ala Asn Tyr Lys Lys Pro Lys Leu
            20                  25

<210> SEQ ID NO 29
<211> LENGTH: 28
<212> TYPE: PRT
<213> ORGANISM: Artificial Sequence
<220> FEATURE:
<223> OTHER INFORMATION: Synthetic peptide

<400> SEQUENCE: 29

Met Ala Asn Leu Gly Tyr Trp Leu Leu Ala Leu Phe Val Thr Met Trp
1               5                   10                  15
Thr Asp Val Gly Leu Cys Lys Lys Arg Pro Lys Pro
            20                  25

<210> SEQ ID NO 30
<211> LENGTH: 24
<212> TYPE: PRT
<213> ORGANISM: Artificial Sequence
<220> FEATURE:
<223> OTHER INFORMATION: Synthetic peptide

<400> SEQUENCE: 30

Leu Gly Thr Tyr Thr Gln Asp Phe Asn Lys Phe His Thr Phe Pro Gln
1               5                   10                  15
Thr Ala Ile Gly Val Gly Ala Pro
            20

<210> SEQ ID NO 31
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 31

Asp Pro Lys Gly Asp Pro Lys Gly Val Thr Val Thr Val Thr Val Thr
1               5                   10                  15
Val Thr Gly Lys Gly Asp Pro Xaa Pro Asp
            20                  25

<210> SEQ ID NO 32
<211> LENGTH: 14
<212> TYPE: PRT
<213> ORGANISM: Artificial Sequence
<220> FEATURE:
<223> OTHER INFORMATION: Synthetic peptide

<400> SEQUENCE: 32

```
Pro Pro Pro Pro Pro Pro Pro Pro Pro Pro Pro Pro
1               5                   10
```

<210> SEQ ID NO 33
<211> LENGTH: 18
<212> TYPE: PRT
<213> ORGANISM: Artificial Sequence
<220> FEATURE:
<223> OTHER INFORMATION: Synthetic peptide

<400> SEQUENCE: 33

```
Val Arg Leu Pro Pro Val Arg Leu Pro Pro Val Arg Leu Pro
1               5                   10                  15

Pro Pro
```

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide

<400> SEQUENCE: 34

```
Pro Arg Pro Leu Pro Pro Pro Arg Pro Gly
1               5                   10
```

<210> SEQ ID NO 35
<211> LENGTH: 30
<212> TYPE: PRT
<213> ORGANISM: Artificial Sequence
<220> FEATURE:
<223> OTHER INFORMATION: Synthetic peptide

<400> SEQUENCE: 35

```
Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30
```

<210> SEQ ID NO 36
<211> LENGTH: 21
<212> TYPE: PRT
<213> ORGANISM: Artificial Sequence
<220> FEATURE:
<223> OTHER INFORMATION: Synthetic peptide

<400> SEQUENCE: 36

```
Thr Arg Ser Ser Arg Ala Gly Leu Gln Phe Pro Val Gly Arg Val His
1               5                   10                  15

Arg Leu Leu Arg Lys
            20
```

<210> SEQ ID NO 37
<211> LENGTH: 23
<212> TYPE: PRT
<213> ORGANISM: Artificial Sequence
<220> FEATURE:
<223> OTHER INFORMATION: Synthetic peptide

<400> SEQUENCE: 37

```
Gly Ile Gly Lys Phe Leu His Ser Ala Lys Lys Phe Gly Lys Ala Phe
1               5                   10                  15

Val Gly Glu Ile Met Asn Ser
            20
```

<210> SEQ ID NO 38
<211> LENGTH: 37
<212> TYPE: PRT
<213> ORGANISM: Artificial Sequence
<220> FEATURE:
<223> OTHER INFORMATION: Synthetic peptide

<400> SEQUENCE: 38

```
Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35
```

<210> SEQ ID NO 39
<211> LENGTH: 28
<212> TYPE: PRT
<213> ORGANISM: Artificial Sequence
<220> FEATURE:
<223> OTHER INFORMATION: Synthetic peptide

<400> SEQUENCE: 39

```
Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25
```

<210> SEQ ID NO 40
<211> LENGTH: 26
<212> TYPE: PRT
<213> ORGANISM: Artificial Sequence
<220> FEATURE:
<223> OTHER INFORMATION: Synthetic peptide

<400> SEQUENCE: 40

```
Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

<210> SEQ ID NO 41
<211> LENGTH: 14
<212> TYPE: PRT
<213> ORGANISM: Artificial Sequence
<220> FEATURE:
<223> OTHER INFORMATION: Synthetic peptide

<400> SEQUENCE: 41

```
Ile Asn Leu Lys Ala Leu Ala Ala Leu Ala Lys Lys Ile Leu
1               5                   10
```

<210> SEQ ID NO 42
<211> LENGTH: 33
<212> TYPE: PRT
<213> ORGANISM: Artificial Sequence
<220> FEATURE:
<223> OTHER INFORMATION: Synthetic peptide

<400> SEQUENCE: 42

```
Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
```

-continued

```
                20                  25                  30
Glu

<210> SEQ ID NO 43
<211> LENGTH: 15
<212> TYPE: PRT
<213> ORGANISM: Artificial Sequence
<220> FEATURE:
<223> OTHER INFORMATION: Synthetic peptide

<400> SEQUENCE: 43

Leu Ala Lys Trp Ala Leu Lys Gln Gly Phe Ala Lys Leu Lys Ser
1               5                   10                  15

<210> SEQ ID NO 44
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 44

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
                20                  25

<210> SEQ ID NO 45
<211> LENGTH: 41
<212> TYPE: PRT
<213> ORGANISM: Artificial Sequence
<220> FEATURE:
<223> OTHER INFORMATION: Synthetic peptide

<400> SEQUENCE: 45

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
                20                  25                  30

Ala Asn Leu Val Pro Arg Thr Glu Ser
        35                  40

<210> SEQ ID NO 46
<211> LENGTH: 20
<212> TYPE: PRT
<213> ORGANISM: Artificial Sequence
<220> FEATURE:
<223> OTHER INFORMATION: Synthetic peptide

<400> SEQUENCE: 46

Leu Lys Lys Leu Leu Lys Lys Leu Leu Lys Lys Leu Leu Lys Lys Leu
1               5                   10                  15

Leu Lys Lys Leu
            20

<210> SEQ ID NO 47
<211> LENGTH: 18
<212> TYPE: PRT
<213> ORGANISM: Artificial Sequence
<220> FEATURE:
<223> OTHER INFORMATION: Synthetic peptide
```

```
<400> SEQUENCE: 47

Lys Leu Lys Leu Lys Leu Lys Leu Lys Leu Lys Leu Lys Leu Lys Leu
1               5                   10                  15

Lys Leu

<210> SEQ ID NO 48
<211> LENGTH: 18
<212> TYPE: PRT
<213> ORGANISM: Artificial Sequence
<220> FEATURE:
<223> OTHER INFORMATION: Synthetic peptide

<400> SEQUENCE: 48

Pro Ala Trp Arg Lys Ala Phe Arg Trp Ala Trp Arg Met Leu Lys Lys
1               5                   10                  15

Ala Ala
```